US006958322B1

(12) United States Patent
Himmelspach et al.

(10) Patent No.: US 6,958,322 B1
(45) Date of Patent: Oct. 25, 2005

(54) FACTOR X ANALOG WITH AN IMPROVED ABILITY TO BE ACTIVATED

(75) Inventors: Michele Himmelspach, Breitstetten (AT); Uwe Schlokat, Orth/Donau (AT)

(73) Assignee: Baxter Aktiengesellschaft, Vienna (AT)

(*) Notice: Subject to any disclaimer, the term of this patent is extended or adjusted under 35 U.S.C. 154(b) by 395 days.

(21) Appl. No.: 09/632,722

(22) Filed: Aug. 4, 2000

(30) Foreign Application Priority Data

Aug. 10, 1999 (AT) .............................. 1377/99

(51) Int. Cl.[7] .............................................. A61K 38/00
(52) U.S. Cl. .............................. 514/12; 514/2; 514/21; 514/8; 435/69.1; 435/69.2; 435/69.6; 435/7.1; 530/350; 530/395; 530/384; 424/94.64
(58) Field of Search ................................ 435/7.1, 69.6, 435/69.1, 69.2; 530/350, 395, 384; 514/12, 2, 8, 21; 424/94.64

(56) References Cited

U.S. PATENT DOCUMENTS

| 4,359,049 A | 11/1982 | Redl et al. |
| 4,501,731 A | 2/1985 | Tishkoff et al. |
| 4,735,616 A | 4/1988 | Eibl et al. |
| 5,460,950 A | 10/1995 | Barr et al. |
| 5,597,799 A | 1/1997 | Wolf |
| 5,635,481 A | 6/1997 | Wolf |
| 5,858,658 A | 1/1999 | Haemmerle et al. |
| 6,210,929 B1 | 4/2001 | Schlokat et al. |
| 6,562,598 B1 | 5/2003 | Himmelspach et al. |
| 6,573,071 B1 * | 6/2003 | Himmelspach et al. .... 435/69.6 |

FOREIGN PATENT DOCUMENTS

| EP | 0 651 054 A1 | 3/1995 |
| WO | WO 94/29370 A1 | 12/1994 |
| WO | WO 98/38317 * | 9/1998 |

OTHER PUBLICATIONS

Bajaj, S. & Mann, K. "Simultaneous Purification of Bovine Prothrombin and Factor X" *J. Biol. Chem.*, Nov. 25, 1973, pp. 7729–7741, vol. 248, No. 22.
Barr, P.J. "Mammalian Subtilisins: The Long–Sought Dibasic Processing Endoproteases" *Cell*, 1991, pp. 1–3, vol. 66.
Clackson, T. et al. *PCR A Practical Approach: General Application of PCR to Gene Cloning and Manipulation*, Eds. McPherson, Quirke and Taylor. 1991, pp. 187–214.
Eby, C.S. et al. "Characterizastion of the Structure and Function of the Carboxy Terminal Peptide of Human Factor X" *Blood*, 1992, pp. 1214, vol. 80, Suppl. 1, Abstract only.
Elsinger, R. *Laboratory Tests of Activated Prothrombin Complex Preparations; Activated Prothrombin Complex Concentrates.* 1982, pp. 77–87 Chapter 11, Eds. Mariani, Russo and Mandelli, Praeger Publishers, U.S.A.
Fair, D.S. and Bahnak, B.R. "Human Hepatoma Cells Secrete Single Chain Factor S. Prothombin and Antithrombin III." *Blood*, Jul. 1984, pp. 194–204, vol. 64, No. 1.

Fischer et al "Structural Analysis of Recombinant von Willebrand Factor: Identification of hetero– and homo–cimers", *FEBS Lett.*, 1994, pp 345–348, vol. 351.
Fung, M. et al. "Characterization of an almost full–length cDNA coding for human blood coagulation factor X" *Proc. Natl. Acad. Sci. USA*, Jun. 1985, pp. 3591–3595, vol. 82.
Giles, A. et al. "A combination of factor Xa and phosphatidvicholine–phosphatidylserine vesicles bypasses factor VIII in vivo." *British J. Haemotology*, 1988, pp. 491–497, vol. 69.
Gordon, V.M. et al. "Proteolytic Activation of Bacterial Toxins by Eukaryotic Cells is Performed by Furin and by Additional Cellular Proteases." *Infec. Immunol.*, 1995, pp. 82–87, vol. 63.
Himmelspach, M. et al. "Alteration of the Specificity of fX Activation by Substitution of Amino Acids Constituting its Activation Site", *XVII Congress of the International Society on Thrombosis and Haemostasis*, 1999, p. 758.
Jesty, J. et al. "The Mechanism of Activation of Factor X Kinetic Control of Alternative Pathways Leading to the Formation of Activated Factor X" *J. Biol. Chem.*, Sep. 10, 1974, pp 5614–5622, vol. 249, No. 17.
Leytus, S. et al. "Characterization of cDNA coding for human factor X" *Proc. Natl. Acad. Sci. USA*, Jun. 1984, pp. 3699–3702, vol. 81.
Leytus, S. et al. "Gene for Human Factor S: A Blood Coagulation Factor Whose Gene Organization is Essentially dentical with that of Factor IX and Protein C" *Biochem.*, 1986, pp. 5098–5102, vol. 25.
Mertens, K. & Bertina, R. "Pathways in the Activation of Human Coagulation Factor X" *Biochem. J.*, 1980, pp. 647–658, vol. 185.
Messier, T. et al. "Cloning and expression in COS–1 cells of a full–length cDNA encoding human coagulation factor X" *Gene*, 1991, pp. 291–294, vol. 99. E sevier.
Moehring, J.M. & Meohring, T.J. "Strains of CHO–K1 Cells Resistant to Pseudomonas Exotoxin A and Cross–Resistant to Diphtheria Toxin and Viruses" *Infection and Immunity*, 1983, pp. 998–1009, vol. 41.
Morita et al. "Structural and Functional Characteristics of a Proteolytically Modified 'Gla Domain–less' Bovine Factor X and Xa (des light chain residues 1–14)." *General Biochem.*, 1980, p. 219, vol. 92, Abstract No. 92:71374k.
Ngo et al. *Computational Complexity, Protein Structure Prediction and the Levinthal Paradox in the Protein Folding Problem and Tertiary Structure.* 1994, Eds. K. Mez. Jr. and Le Grand, Birkhauser, Boston.

(Continued)

*Primary Examiner*—Jon Weber
*Assistant Examiner*—Hope A. Robinson
(74) *Attorney, Agent, or Firm*—Townsend and Townsend and Crew LLP

(57) ABSTRACT

This invention describes a factor Xa analog which has a substitution of a minimum of one of the amino acid between Glu226 and Arg234 and possibly Ile235, relative to the amino acid numbering according to FIG. 1, a preparation containing the activated form of the factor X analog, and a method for the production of these molecules.

29 Claims, 6 Drawing Sheets

OTHER PUBLICATIONS

Ohnishi Y. et al. "A Furin–Defective Cell Line is Able to Process Correctly the gp160 of Human Immunodeficiency Virus Type 1." *J. Virol.*, 1994, pp. 4075–4079, vol. 68.

Pryzdial, E. & Kessler, G. "Autoproteolysis or Plasmin–mediated Cleavage of Factor Xaα Exposes a Plasminogen Binding Site and Inhibits Coagulation." *J. Biol. Chem.*, Jul. 12, 1996, pp. 16614–16620, vol. 271 No. 28.

Pryzdial, E. & Kessler, G. "Kinetics of Blood Coagulation oFactor Xaα Autoprotcolytic Conversion of Factor Xaβ" *J. Biol. Chem.*, Jul. 12, 1996, pp. 16621–16626, vol. 271, No. 28.

Rehemtulla, A. & Kaufman, R.J. "Preferred Sequence Requirements for Cleavage of Pro–von Willebrand Factor by Propeptide–Processing Enzymes." *Blood*, 1992, pp. 2349–2355, vol. 79.

Rudolph, A.E. et al. "Expression, Purification and Characterization of Recombinant Human Factor X[1]." *Protein Expression and Purification*, 1997 pp. 373–378, vol. 10.

Sherrill, G.B. et al. "Inactivation of Human Blood Coagulation Factor X by Chemical Modification of Gamma–Carboxyglutamic Acid Residues,"0 *Enzymes*, 1985, p. 239, vol. 102, Abstract No. 102:2489q.

Teng. C. & Seegers, W. "Production of factor X and factor Xa variants with thrombin, acutin and by autolysis." *Thrombosis Research* 1981, pp. 213–220, vol. 22.

Urlaub, G. & Chasin, L. "Isolation of Chinese hamster cell mutants deficient in dihydrofolate reductase activity." *Proc. Natl. Acad. Sci. USA*, Jul. 1980, pp. 4216–4220, vol. 77, No. 7.

Wallin, R. et al. "Intracellular Proteolytic Processing of the Two–Chain Vitamin K–Dependent Coagulation Factor X" *Thrombosis Res.*, 1994, pp. 395–403, vol. 73.

Watzke, H. & High, K "Factor X " *Molecular Basis of Thrombosis and Hemostasis*, 1995, pp. 239–255, Chapter 11, Eds. High and Roberts.

Wells et al. "Additivity of Mutational Effects In Proteins." *Biochemistry*, 1990, pp. 8509–8517, vol. 29, No. 37.

Wolf, D. et al. "Design of Constructs for the Expression of Biologically Active Recombinant Human Factors X and Xa" *J. Biol. Chem.*, Jul. 25, 1991, pp. 13726–13730, vol. 266, No. 21.

\* cited by examiner

```
                                    (-40)
                                      1
                     Met Gly Arg Pro Leu His Leu Val Leu Leu Ser Ala Ser Leu Ala Gly Leu Leu Leu
                     ATG GGG CGC CCA CTG CAC CTC GTC CTG CTC AGT GCC TCC CTG GCT GGC CTC CTG CTG
                                  9              18              27              36              45              54
                                                                                                  (-4)            (-1)
                                                                                                                   40
Leu Gly Glu Ser Leu Phe Ile Arg Arg Glu Gln Ala Asn Asn Ile Leu Ala Arg Val Thr Arg
CTC GGG GAA AGT CTG TTC ATC CGC AGG GAG CAG GCC AAC AAC ATC CTG GCG AGG GTC ACG AGG
             66              75              84              93             102             111             120

(+1)
 41
Ala Asn Ser Phe Leu Glu Glu Met Lys Lys Gly His Leu Glu Arg Glu Cys Met Glu Glu Thr
GCC AAT TCC TTT CTT GAA GAG ATG AAG AAA GGA CAC CTC GAA AGA GAG TGC ATG GAA GAG ACC
            129             138             147             156             165             174             183

Cys Ser Tyr Glu Glu Ala Arg Glu Val Phe Glu Asp Ser Asp Lys Thr Asn Glu Phe Trp Asn
TGC TCA TAC GAA GAG GCC CGC GAG GTC TTT GAG GAC AGC GAC AAG ACG AAT GAA TTC TGG AAT
            192             201             210             219             228             237             246

Lys Tyr Lys Asp Gly Asp Gln Cys Glu Thr Ser Pro Cys Gln Asn Gln Gly Lys Cys Lys Asp
AAA TAC AAA GAT GGC GAC CAG TGT GAG ACC AGT CCT TGC CAG AAC CAG GGC AAA TGT AAA GAC
            255             264             273             282             291             300             309

Gly Leu Gly Glu Tyr Thr Cys Thr Cys Leu Glu Gly Phe Glu Gly Lys Asn Cys Glu Leu Phe
GGC CTC GGG GAA TAC ACC TGC ACC TGT TTA GAA GGA TTC GAA GGC AAA AAC TGT GAA TTA TTC
            318             327             336             345             354             363             372

Thr Arg Lys Leu Cys Ser Leu Asp Asn Gly Asp Cys Asp Gln Phe Cys His Glu Glu Gln Asn
ACA CGG AAG CTC TGC AGC CTG GAC AAC GGG GAC TGT GAC CAG TTC TGC CAC GAG GAA CAG AAC
            381             390             399             408             417             426             435

Ser Val Val Cys Ser Cys Ala Arg Gly Tyr Thr Leu Ala Asp Asn Gly Lys Ala Cys Ile Pro
TCT GTG GTG TGC TCC TGC GCC CGC GGG TAC ACC CTG GCT GAC AAC GGC AAG GCC TGC ATT CCC
            444             453             462             471             480             489             498

178 179 180 181 182 183
Thr Gly Pro Tyr Pro Cys Gly Lys Gln Thr Leu Glu Arg Arg Lys Arg Ser Val Ala Gln Ala
ACA GGG CCC TAC CCC TGT GGG AAA CAG ACC CTG GAA CGC AGG AAG AGG TCA GTG GCC CAG GCC
            507             516             525             534             543             552             561

Thr Ser Ser Ser Gly Glu Ala Pro Asp Ser Ile Thr Trp Lys Pro Tyr Asp Ala Ala Asp Leu
ACC AGC AGC AGC GGG GAG GCC CCT GAC AGC ATC ACA TGG AAG CCA TAT GAT GCA GCC GAC CTG
            570             579             588             597             606             615             624

R6
                                                                                                                229
Asp Pro Thr Glu Asn Pro Phe Asp Leu Leu Asp Phe Asn Gln Thr Gln Pro Glu Arg Gly Asp
GAC CCC ACC GAG AAC CCC TTC GAC CTG CTT GAC TTC AAC CAG ACG CAG CCT GAG AGG GGC GAC
            633             642             651             660             669             678             687

R5  R4  R3  R2      R1
                 234 235
Asn Asn Leu Thr Arg Ile Val Gly Gly Gln Glu Cys Lys Asp Gly Glu Cys Pro Trp Gln Ala
AAC AAC CTC ACC AGG ATC GTG GGA GGC CAG GAA TGC AAG GAC GGG GAG TGT CCC TGG CAG GCC
            696             705             714             723             732             741             750
```

Fig. 1A

```
Leu Leu Ile Asn Glu Glu Asn Glu Gly Phe Cys Gly Gly Thr Ile Leu Ser Glu Phe Tyr Ile
CTG CTC ATC AAT GAG GAA AAC GAG GGT TTC TGT GGT GGA ACT ATT CTG AGC GAG TTC TAC ATC
        759         768         777         786         795         804         813

Leu Thr Ala Ala His Cys Leu Tyr Gln Ala Lys Arg Phe Lys Val Arg Val Gly Asp Arg Asn
CTA ACG GCA GCC CAC TGT CTC TAC CAA GCC AAG AGA TTC AAG GTG AGG GTA GGG GAC CGG AAC
        822         831         840         849         858         867         876

Thr Glu Gln Glu Glu Gly Gly Glu Ala Val His Glu Val Glu Val Val Ile Lys His Asn Arg
ACG GAG CAG GAG GAG GGC GGT GAG GCG GTG CAC GAG GTG GAG GTG GTC ATC AAG CAC AAC CGG
        885         894         903         912         921         930         939

Phe Thr Lys Glu Thr Tyr Asp Phe Asp Ile Ala Val Leu Arg Leu Lys Thr Pro Ile Thr Phe
TTC ACA AAG GAG ACC TAT GAC TTC GAC ATC GCC GTG CTC CGG CTC AAG ACC CCC ATC ACC TTC
        948         957         966         975         984         993        1002

Arg Met Asn Val Ala Pro Ala Cys Leu Pro Glu Arg Asp Trp Ala Glu Ser Thr Leu Met Thr
CGC ATG AAC GTG GCG CCT GCC TGC CTC CCC GAG CGT GAC TGG GCC GAG TCC ACG CTG ATG ACG
       1011        1020        1029        1038        1047        1056        1065

Gln Lys Thr Gly Ile Val Ser Gly Phe Gly Arg Thr His Glu Lys Gly Arg Gln Ser Thr Arg
CAG AAG ACG GGG ATT GTG AGC GGC TTC GGG CGC ACC CAC GAG AAG GGC CGG CAG TCC ACC AGG
       1074        1083        1092        1101        1110        1119        1128

Leu Lys Met Leu Glu Val Pro Tyr Val Asp Arg Asn Ser Cys Lys Leu Ser Ser Ser Phe Ile
CTC AAG ATG CTG GAG GTG CCC TAC GTG GAC CGC AAC AGC TGC AAG CTG TCC AGC AGC TTC ATC
       1137        1146        1155        1164        1173        1182        1191

Ile Thr Gln Asn Met Phe Cys Ala Gly Tyr Asp Thr Lys Gln Glu Asp Ala Cys Gln Gly Asp
ATC ACC CAG AAC ATG TTC TGT GCC GGC TAC GAC ACC AAG CAG GAG GAT GCC TGC CAG GGG GAC
       1200        1209        1218        1227        1236        1245        1254

Ser Gly Gly Pro His Val Thr Arg Phe Lys Asp Thr Tyr Phe Val Thr Gly Ile Val Ser Trp
AGC GGG GGC CCG CAC GTC ACC CGC TTC AAG GAC ACC TAC TTC GTG ACA GGC ATC GTC AGC TGG
       1263        1272        1281        1290        1299        1308        1317

Gly Glu Ser Cys Ala Arg Lys Gly Lys Tyr Gly Ile Tyr Thr Lys Val Thr Ala Phe Leu Lys
GGA GAG AGC TGT GCC CGT AAG GGG AAG TAC GGG ATC TAC ACC AAG GTC ACC GCC TTC CTC AAG
       1326        1335        1344        1353        1362        1371        1380

469 470                 475 476             480
Trp Ile Asp Arg Ser Met Lys Thr Arg Gly Leu Pro Lys Ala Lys Ser His Ala Pro Glu Val
TGG ATC GAC AGG TCC ATG AAA ACC AGG GGC TTG CCC AAG GCC AAG AGC CAT GCC CCG GAG GTC
       1389        1398        1407        1416        1425        1434        1443

488
Ile Thr Ser Ser Pro Leu Lys TER
ATA ACG TCC TCT CCA TTA AAG TGA
       1452        1461    1467
```

Fig. 1B

SEQUENCE LISTING

```
<160> NUMBER OF SEQ ID NOS: 18

<210> SEQ ID NO 1
<211> LENGTH: 1467
<212> TYPE: DNA
<213> ORGANISM: Homo sapiens
<220> FEATURE:
<221> NAME/KEY: CDS
<222> LOCATION: (1)..(1467)
<223> OTHER INFORMATION: factor X

<400> SEQUENCE: 1 atg ggg cgc cca ctg cac ctc gtc ctg ctc agt gcc tcc ctg gct ggc        48
Met Gly Arg Pro Leu His Leu Val Leu Leu Ser Ala Ser Leu Ala Gly
 1               5                  10                  15 ctc ctg ctc ctc ggg gaa agt ctg ttc atc cgc agg gag cag gcc aac        96
Leu Leu Leu Leu Gly Glu Ser Leu Phe Ile Arg Arg Glu Gln Ala Asn
            20                  25                  30 aac atc ctg gcg agg gtc acg agg gcc aat tcc ttt ctt gaa gag atg       144
Asn Ile Leu Ala Arg Val Thr Arg Ala Asn Ser Phe Leu Glu Glu Met
        35                  40                  45
```

```
aag aaa gga cac ctc gaa aga gag tgc atg gaa gag acc tgc tca tac     192
Lys Lys Gly His Leu Glu Arg Glu Cys Met Glu Glu Thr Cys Ser Tyr
     50                  55                  60 gaa gag gcc cgc gag gtc ttt gag gac agc gac aag acg aat gaa ttc     240
Glu Glu Ala Arg Glu Val Phe Glu Asp Ser Asp Lys Thr Asn Glu Phe
 65                  70                  75                  80 tgg aat aaa tac aaa gat ggc gac cag tgt gag acc agt cct tgc cag     288
Trp Asn Lys Tyr Lys Asp Gly Asp Gln Cys Glu Thr Ser Pro Cys Gln
                 85                  90                  95 aac cag ggc aaa tgt aaa gac ggc ctc ggg gaa tac acc tgc acc tgt     336
Asn Gln Gly Lys Cys Lys Asp Gly Leu Gly Glu Tyr Thr Cys Thr Cys
            100                 105                 110 tta gaa gga ttc gaa ggc aaa aac tgt gaa tta ttc aca cgg aag ctc     384
Leu Glu Gly Phe Glu Gly Lys Asn Cys Glu Leu Phe Thr Arg Lys Leu
            115                 120                 125 tgc agc ctg gac aac ggg gac tgt gac cag ttc tgc cac gag gaa cag     432
Cys Ser Leu Asp Asn Gly Asp Cys Asp Gln Phe Cys His Glu Glu Gln
        130                 135                 140 aac tct gtg gtg tgc tcc tgc gcc cgc ggg tac acc ctg gct gac aac     480
Asn Ser Val Val Cys Ser Cys Ala Arg Gly Tyr Thr Leu Ala Asp Asn
145                 150                 155                 160 ggc aag gcc tgc att ccc aca ggg ccc tac ccc tgt ggg aaa cag acc     528
Gly Lys Ala Cys Ile Pro Thr Gly Pro Tyr Pro Cys Gly Lys Gln Thr
                165                 170                 175 ctg gaa cgc agg aag agg tca gtg gcc cag gcc acc agc agc agc ggg     576
Leu Glu Arg Arg Lys Arg Ser Val Ala Gln Ala Thr Ser Ser Ser Gly
            180                 185                 190 gag gcc cct gac agc atc aca tgg aag cca tat gat gca gcc gac ctg     624
Glu Ala Pro Asp Ser Ile Thr Trp Lys Pro Tyr Asp Ala Ala Asp Leu
        195                 200                 205 gac ccc acc gag aac ccc ttc gac ctg ctt gac ttc aac cag acg cag     672
Asp Pro Thr Glu Asn Pro Phe Asp Leu Leu Asp Phe Asn Gln Thr Gln
210                 215                 220 cct gag agg ggc gac aac aac ctc acc agg atc gtg gga ggc cag gaa     720
Pro Glu Arg Gly Asp Asn Asn Leu Thr Arg Ile Val Gly Gly Gln Glu
225                 230                 235                 240 tgc aag gac ggg gag tgt ccc tgg cag gcc ctg ctc atc aat gag gaa     768
Cys Lys Asp Gly Glu Cys Pro Trp Gln Ala Leu Leu Ile Asn Glu Glu
                245                 250                 255 aac gag ggt ttc tgt ggt gga act att ctg agc gag ttc tac atc cta     816
Asn Glu Gly Phe Cys Gly Gly Thr Ile Leu Ser Glu Phe Tyr Ile Leu
            260                 265                 270 acg gca gcc cac tgt ctc tac caa gcc aag aga ttc aag gtg agg gta     864
Thr Ala Ala His Cys Leu Tyr Gln Ala Lys Arg Phe Lys Val Arg Val
        275                 280                 285 ggg gac cgg aac acg gag cag gag gag ggc ggt gag gcg gtg cac gag     912
Gly Asp Arg Asn Thr Glu Gln Glu Glu Gly Gly Glu Ala Val His Glu
    290                 295                 300 gtg gag gtg gtc atc aag cac aac cgg ttc aca aag gag acc tat gac     960
Val Glu Val Val Ile Lys His Asn Arg Phe Thr Lys Glu Thr Tyr Asp
305                 310                 315                 320 ttc gac atc gcc gtg ctc cgg ctc aag acc ccc atc acc ttc cgc atg    1008
Phe Asp Ile Ala Val Leu Arg Leu Lys Thr Pro Ile Thr Phe Arg Met
                325                 330                 335 aac gtg gcg cct gcc tgc ctc ccc gag cgt gac tgg gcc gag tcc acg    1056
Asn Val Ala Pro Ala Cys Leu Pro Glu Arg Asp Trp Ala Glu Ser Thr
            340                 345                 350 ctg atg acg cag aag acg ggg att gtg agc ggc ttc ggg cgc acc cac    1104
Leu Met Thr Gln Lys Thr Gly Ile Val Ser Gly Phe Gly Arg Thr His
```

-continued

```
                      355                 360                 365
gag aag ggc cgg cag tcc acc agg ctc aag atg ctg gag gtg ccc tac      1152
Glu Lys Gly Arg Gln Ser Thr Arg Leu Lys Met Leu Glu Val Pro Tyr
        370                 375                 380 gtg gac cgc aac agc tgc aag ctg tcc agc agc ttc atc atc acc cag      1200
Val Asp Arg Asn Ser Cys Lys Leu Ser Ser Ser Phe Ile Ile Thr Gln
385                 390                 395                 400 aac atg ttc tgt gcc ggc tac gac acc aag cag gag gat gcc tgc cag      1248
Asn Met Phe Cys Ala Gly Tyr Asp Thr Lys Gln Glu Asp Ala Cys Gln
                405                 410                 415 ggg gac agc ggg ggc ccg cac gtc acc cgc ttc aag gac acc tac ttc      1296
Gly Asp Ser Gly Gly Pro His Val Thr Arg Phe Lys Asp Thr Tyr Phe
        420                 425                 430 gtg aca ggc atc gtc agc tgg gga gag agc tgt gcc cgt aag ggg aag      1344
Val Thr Gly Ile Val Ser Trp Gly Glu Ser Cys Ala Arg Lys Gly Lys
435                 440                 445 tac ggg atc tac acc aag gtc acc gcc ttc ctc aag tgg atc gac agg      1392
Tyr Gly Ile Tyr Thr Lys Val Thr Ala Phe Leu Lys Trp Ile Asp Arg
                450                 455                 460 tcc atg aaa acc agg ggc ttg ccc aag gcc aag agc cat gcc ccg gag      1440
Ser Met Lys Thr Arg Gly Leu Pro Lys Ala Lys Ser His Ala Pro Glu
465                 470                 475                 480 gtc ata acg tcc tct cca tta aag tga                                  1467
Val Ile Thr Ser Ser Pro Leu Lys
                485
```

<210> SEQ ID NO 2
<211> LENGTH: 488
<212> TYPE: PRT
<213> ORGANISM: Homo sapiens
<220> FEATURE:
<223> OTHER INFORMATION: factor X

<400> SEQUENCE: 2

```
Met Gly Arg Pro Leu His Leu Val Leu Leu Ser Ala Ser Leu Ala Gly
 1               5                  10                  15

Leu Leu Leu Leu Gly Glu Ser Leu Phe Ile Arg Arg Glu Gln Ala Asn
                20                  25                  30

Asn Ile Leu Ala Arg Val Thr Arg Ala Asn Ser Phe Leu Glu Glu Met
            35                  40                  45

Lys Lys Gly His Leu Glu Arg Glu Cys Met Glu Glu Thr Cys Ser Tyr
        50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190
```

```
Glu Ala Pro Asp Ser Ile Thr Trp Lys Pro Tyr Asp Ala Ala Asp Leu
            195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
            245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
            275                 280                 285

Gly Asp Arg Asn Thr Glu Gln Glu Glu Gly Gly Glu Ala Val His Glu
            290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
            325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
            405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Ser Cys Ala Arg Lys Gly Lys
            435                 440                 445

Tyr Gly Ile Tyr Thr Lys Val Thr Ala Phe Leu Lys Trp Ile Asp Arg
            450                 455                 460

Ser Met Lys Thr Arg Gly Leu Pro Lys Ala Lys Ser His Ala Pro Glu
465                 470                 475                 480

Val Ile Thr Ser Ser Pro Leu Lys
            485

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:PCR 5'
      primer oligonucleotide #2911

<400> SEQUENCE: 3
attactcgag aagcttacca tgggcgcc actg                                  34

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:PCR 3'
      primer oligonucleotide #2912
```

```
<400> SEQUENCE: 4
attacaattg ctgcagggat ccac                                              24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:PCR 5'
      primer oligonucleotide #4211

<400> SEQUENCE: 5
ggcaaggcct gcattcccac a                                                 21

<210> SEQ ID NO 6
<211> LENGTH: 55
<212> TYPE: DNA
<213> ORGANISM: Artificial Sequence
<220> FEATURE:
<223> OTHER INFORMATION: Description of Artificial Sequence:PCR 3'
      primer oligonucleotide #5039

<400> SEQUENCE: 6
gcgctcccac gatcctggtg aagtcattaa agctttgctc aggctgcgtc tggtt            55

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence:factor IX
      protease cutting site in the region of the activation peptide

<400> SEQUENCE: 7

Gln Ser Phe Asn Asp Phe Thr Arg Val Val Gly Gly
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:factor X
      protease cutting site in the region of the activation peptide

<400> SEQUENCE: 8

Arg Gly Asp Asn Asn Leu Thr Arg Ile Val Gly Gly
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence:factor X
      analog fX/fXIa(Q-R/I) protease cutting site in the region
      of the activation peptide

<400> SEQUENCE: 9

Gln Ser Phe Asn Asp Phe Thr Arg Ile Val Gly Gly
 1               5                  10

<210> SEQ ID NO 10
<211> LENGTH: 10
<212> TYPE: PRT
<213> ORGANISM: Artificial Sequence
```

```
<220> FEATURE:
<223> OTHER INFORMATION: Description of Artificial Sequence:factor X
      region of amino acids 226-234

<400> SEQUENCE: 10

Glu Arg Gly Asp Asn Asp Phe Thr Arg Ile
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:factor X
      analog modified in the activation peptide

<400> SEQUENCE: 11

Glu Gln Ser Asp Asn Asp Leu Thr Arg Val
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:factor X
      analog modified in the activation peptide

<400> SEQUENCE: 12

Glu Gln Ser Asp Asn Asp Leu Thr Arg Ile
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:factor X
      analog modified in the activation peptide

<400> SEQUENCE: 13

Glu Ser Gln Thr Ser Lys Leu Thr Arg Val
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:factor X
      analog modified in the activation peptide

<400> SEQUENCE: 14

Glu Ser Gln Thr Ser Lys Leu Thr Arg Ile
 1               5                  10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:factor X
      position 227-234

<400> SEQUENCE: 15

Arg Gly Asp Asn Asn Leu Thr Arg Ile
 1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:Q-R/I

<400> SEQUENCE: 16

Gln Ser Phe Asn Asp Phe Thr Arg Ile
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:factor X
      analog modification in the region of amino acids 227-233

<400> SEQUENCE: 17

Gln Ser Phe Asn Asp Phe Thr
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:factor X
      analog modification in the region of amino acids 227-233

<400> SEQUENCE: 18

Ser Gln Thr Ser Lys Leu Thr
 1               5
```

FACTOR X ANALOG WITH AN IMPROVED ABILITY TO BE ACTIVATED

This application claims priority under 35 U.S.C. 119 (a–d) to Application No. A 1377/99, filed on Aug. 10, 1999.

FIELD OF THE INVENTION

The present invention relates to factor X analogs with an enhanced ability to be activated by means of a substitution in the region of the activation peptide, a preparation containing the factor X analogs according to the present invention, and a method for the production of single-chain and double-chain factor X analogs.

BACKGROUND OF THE INVENTION

Once the blood coagulation process has been initiated, the coagulation cascade goes through the stages of sequentially activating various proenzymes (zymogens) in the blood into their active forms, the serine proteases. This includes, among others, factor XII/XIIa, factor XII/XIa, factor IX/IXa, factor XIXa, factor VII/VIIa, and prothrombin/thrombin. Most of these enzymes are active in the physiological state only if they are associated in a complex on a membrane surface. Ca ions are involved in many of these processes. Blood coagulation follows either the intrinsic pathway, in which case all protein components are present in the blood, or the extrinsic pathway, in which the cell membrane tissue factor plays a critical role. Closure of the wound finally takes place as a result of the conversion of fibrinogen into fibrin through the action of thrombin.

The prothrombinase complex is responsible for activating prothrombin to form thrombin. Thrombin is an important enzyme which can act both as a procoagulant and as an anticoagulant. The prothrombinase complex, in which, among others, factor Va (as a cofactor) and factor Xa (as serine protease) participate, assembles in a Ca-dependent association on the surface of phospholipids. It is hypothesized that the catalytic component of the prothrombinase complex is factor Xa.

Factor X (also called Stuart-Prower factor or Prower factor) is a vitamin K-dependent coagulation glycoprotein which participates in the intrinsic and extrinsic blood coagulation cascade. The primary translation product of factor X (pre-pro-FX) contains 488 amino acids and is synthesized by the liver of by human hepatoma cells first as a single-chain 75 kD precursor protein. In the plasma, factor X is present mainly as a double-chain molecule (Fair et al., Blood 64 (1984), pp. 194–204).

During the biosynthesis, after cleavage of the presequence by a signal peptidase (between Ser23 and Leu24) and the propeptide (between Arg40 and Ala41), the single-chain factor X molecule is cleaved by processing and deletion of the tripeptide Argl 80-Lysl 81-Arg 182 into the double-chain form which comprises an approximately 22 kD light chain and an approximately 50 kD heavy chain, the two chains being connected by way of a disulfide bridge (FIG. 1). Factor X therefore circulates in the plasma as a double-chain molecule.

During the blood coagulation process, factor X is converted from the inactive zymogen into active protease factor Xa through limited proteolytic action, in the course of which the activation of factor X to form Factor Xa can take place in one of 2 membrane-bound complexes: the extrinsic factor VIIa/tissue factor complex or the intrinsic factor VIIIa/factor IXa phospholipid Ca complex, the so-called "tenase complex" (Mertens et al., Biochem. J. 185 (1980), pp. 647–658).

A proteolytic cleavage between amino acids Arg234 and Ile235 leads to the release of a 52 amino acids long activation peptide from the N-terminus of the heavy chain and thus to the formation of the active enzyme, factor Xa. The catalytic center of factor Xa is located on the heavy chain.

The activation via the factor VIIa-TF (extrinsic) complex leads to the formation of factor Xaα (35 kD) and factor Xaβ (31 kD), and, if the concentrations of factor VIIa in the complex are low, a polypeptide of 42 kD is present as well.

The formation of factor Xaα takes place via a cleavage at Arg234/Ile 235 of the heavy chain and represents the activation of factor X to form factor Xa. The presence of factor Xaβ presumably results from an autocatalytic cleavage at Arg469/Gly470 in the C-terminus of the heavy chain of factor Xaα and the cleavage of a 4.5 kD peptide. Like factor Xaα, factor Xaβ also has catalytic activity. It was shown, however, that during the cleavage of factor Xaα to form Xaβ, a plasminogen receptor binding site forms and that factor Xaβ may also have fibrinolytic activity and may participate as a cofactor in the fibrinolysis. The conversion of factor Xaα into factor Xaβ, however, proceeds more slowly than the formation of thrombin, as a result of which the initiation of the fibrinolysis prior to the formation of a blood clot is prevented (Pryzdial et al., J. Biol. Chen 271 (1996), pp. 16614–16620; Pryzdial et al., J. Biol. Chem. 271 (1996), pp. 16621–16626).

The 42 kD polypeptide results from a processing in the C terminus of the heavy chain between Arg426 and Gly470 without prior processing between Arg234 and lie 235. Like a factor Xaγ fragment, this intermediate which forms as a result of proteolysis at Lys370 also does not have any catalytic activity (Mertens et al., Biochem. J. 185 (1980), pp. 647–658; Pryzdial et al., J. Biol. Chem. 271 (1996), pp. 16614–16620).

The activation of factor X in the intrinsic pathway is catalyzed by the factor IXa-fctor VIIIa complex. During the activation, the same processing products are obtained, but the factor Xaβ product is obtained in a greater yield than other factor X processing products (Jesty et al., J. Biol. Chem. 249 (1974), p. 5614).

In vitro, factor X can be activated, for example, by means of Russell's Viper Venom (RVV) or trypsin (Bajaj et al., J. Biol. Chem. 248, (1973), pp. 7729–7741) or purified physiological activators, such as FVIIa/TF complex or factor IXa/factor VIIIa complex (Mertens et al., Biochem. J. 185 (1980), pp. 647–658).

In most cases, commercially available factor X products from plasma contain a mixture of factor Xaα and factor Xaβ since after the activation of factor X to form factor Xa, primarily factor Xaα forms, which, in turn, is cleaved in an autocatalytic process to form factor Xaβ.

To produce a uniform factor Xa product with a high molecular integrity, EP 0 651 054 proposed that factor X be activated over a relatively long period of time with RVV, with the result that the resulting final product contained mainly factor Xaβ. Both the by-products, for example, factor Xaα, and the protease were subsequently removed in several chromatographic steps.

The cDNA for factor X was isolated and characterized (Leytus et al., Proc. Natl. Acad. Sci. USA 82 (1984), pp. 3699–3702; Fung et al., Proc. Natl. Acad. Sci. USA 82 (1985), pp. 3591–3595). Human factor X was expressed in vitro in various cell types, such as human embryonal kidney cells or CHO cells (Wolf et al., J. Biol. Chem. 266 (1991), pp. 13726–13730). It was found, however, that in the recombinant expression of human factor X, in contrast to the in vivo situation, the processing in position Arg40/Ala41 is inefficient and that different N termini form on the light chain of factor X (Wolf et al., J. Biol. Chem. 266 (1991), pp. 13726–13730). In vitro, recombinant factor X (rFX) was activated by means of RVV to form recombinant factor Xa (rFXa) or rFXa was directly expressed, in the course of which the activation peptide of amino acid 183 to amino acid 234 was deleted and replaced with a tripeptide to enable processing directly into a double-chain rFXa form. Approximately 70% of the purified rFX were processed to form a light and a heavy chain, and the remaining 30% constituted single-chain rFX with 75 kD. Although the direct expression or rFXa did lead to the formation of active factor Xa, it also led to inactive intermediates. In addition, Wolf et al. (J. Biol. Chem. 266 (1991), pp. 13726–13730) also observed a decreased activity of recombinant factor X, which they attributed to the inferior activation ability of rFX through RVV and to the inactive population of proteins and polypeptides of the single-chain precursor molecule. In particular, they found that rFXa, when expressed by recombinant cells, is highly unstable, which they attributed to the high autoproteolytic rate.

WO 98/38317 describes factor X analogs, in which the amino acids can be modified between Glu228 and Arg234, as a result of which these constructs can be activated, for example, by proteases, such as furin.

To study the function of the C-terminal peptide of factor Xaα, Eby et al. (Blood 80 (Suppl. 1) (1992), pp. 1214 A) introduced a stop codon in position Gly430 of the factor X sequence. They did not, however, find a difference between the activation rate of factor Xa (FXaα) with a β-peptide and a deletion mutant without a β-peptide (FXaB).

Factor Xa is an important component of the prothrombinase complex and is therefore used for the quick arrest of bleeding as well as in patients with blood coagulation disorders, such as hemophilia. Especially in the treatment of patients suffering from hemophilia, which is characterized by a factor VIII or a factor IX deficiency, with factor concentrates that are produced from plasma, a complication that frequently arises is that inhibitory antibodies to these factors are formed. Therefore, a number of alternatives were developed to treat patients suffering from hemophilia with factors with a bypass activity. Thus, for example, the use of prothrombin complex concentrate, partially activated protirombinase complex (APPC), factor VIIa, or FEIBA has been proposed. Commercial preparations with factor VIII inhibitory bypass activity include, for example, FEIBA® or Autoplex®. FEIBA, for example, contains comparable units of factor II, factor VII, factor IX, factor X, and FEIBA, small quantities of factor VIII and factor V, and traces of activated coagulation factors, such as thrombin and factor Xa and/or a factor with factor Xa-like activity (Elsinger, Activated Prothrombin Complex Concentrates. Eds. Marian Russo, Mandelli (1982), pp. 77–87). Elsinger especially stresses the importance of a "factor Xa-like" activity in FEIBA. The factor VIII inhibitory bypass activity was demonstrated by Giles et al. (British J. Hematology 9 (1988), pp. 491–497) in the animal model in particular for a combination of purified factor Xa and phospholipids.

Thus, there is a considerable need and a number of different fields of application for factor X/Xa or factor X/Xa-like proteins, either by themselves or as a component of a coagulation complex in hemostatic therapy. Compared to the half-life of zymogen, the half-life of factor Xa is considerably reduced both in vivo and in vitro. Thus, for example, factor X can be stably stored in glycerol for 18 months while under the same conditions, factor Xa is stable only for 5 months (Bajaj et al., J. Biol. Chem. 248 (1973), pp. 7729–2241), or, if stored in glycerol at 4° C. for 8 months, it shows a reduction of the activity by more than 60% (Teng et al., Thrombosis Res. 22 (1981), pp. 213–220). In serum, the half-life of factor Xa is only 30 seconds.

Due to the instability of factor Xa, it has been proposed that factor X preparations be administered (U.S. Pat. No. 4,501,731). In cases of life-threatening bleeding, in particular in patients suffering from hemophilia, however, an administration of factor X has no effect since, due to the lack of the functional "tenase complex," it is not possible for an effective activation of factor X into factor Xa to take place in the intrinsic blood coagulation pathway and since an activation by way of the extrinsic pathway often takes place too slowly to have a rapid effect. Furthermore, patients suffering from hemophilia have a sufficient supply of factor X; however, compared to factor Xa, factor X has a pro-thrombinase activity that is 1000 times lower. In cases of this type, activated factor Xa must be administered directly, possibly in combination with phospholipids, such as described by Giles et al. (British J.

Haematology 9 (1988). pp. 491–497), or with other coagulation factors, for example, with factor VIII inhibitory bypass activity.

In the production of factor Xa from factor X, the activation has so far been triggered mainly by means of nonphysiological activators of animal origin, such as RVV or trypsin, but this means that care has to be taken to ensure with absolute certainty that the final product is completely free from these proteases. As already mentioned above, during the activation of factor X to factor Xa, a large number of inactive intermediates is formed (Bajaj et al., J. Biol. Chem. 248 (1973), pp. 7729–7741, Mertens et al., Biochem. J. 185 (1980), pp. 647–658). The presence of such intermediates leads to a decrease of the specific activity of the product and potentially even to the type of intermediates that might serve as antagonists of the active serine protease. Thus, to produce a uniform, pure product with a high specific activity by means of conventional methods, time-consuming and complicated procedures for the activation and chromatographic purification are required.

SUMMARY OF THE INVENTION

The present invention provides a preparation which contains a polypeptide with factor X/Xa activity, which, compared to prior art, can be more readily activated by factor XIa or a derivative thereof, which has a high stability, and which can be activated by means of factor XIa or a derivative thereof, without having to use one of the proteases used in prior art to activate the natural factor X, particularly one of animal origins, such as RVV or trypsin. Another objective of the present invention is to make available a pharmaceutical preparation with factor VIII inhibitory bypass activity.

BRIEF DESCRIPTION OF THE DRAWINGS

FIG. 1A and 1B present the nucleotide and amino acid sequence of factor X (SEQ ID NOS: 1 and 2).

DETAILED DESCRIPTION OF THE INVENTION

Figure 2:
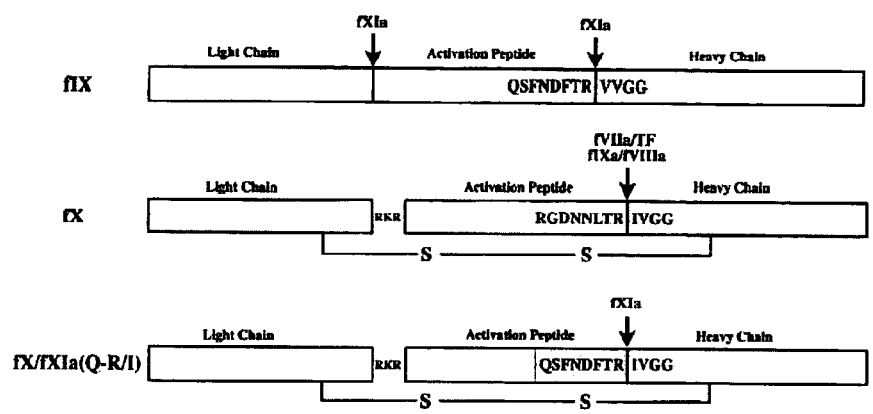
FIG. 2 is a diagrammatic representation of the factor X analog with a modified protease cutting site in the region of the activation peptide (SEQ ID NOS:7–9)
Figure 3:
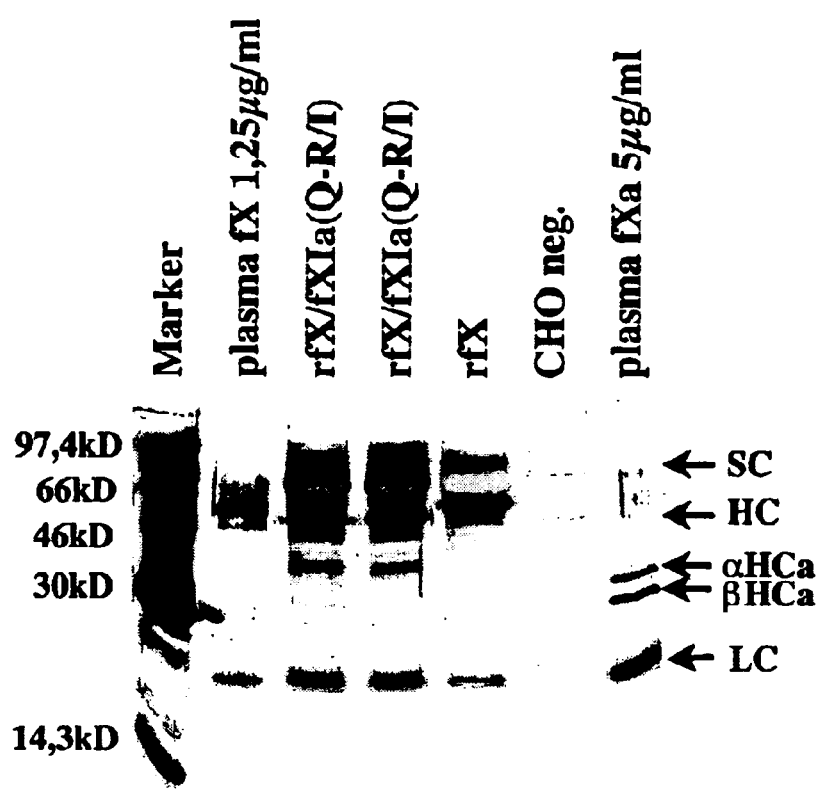
FIG. 3 shows a Western blot analysis of recombinant factor X expressed in CHO cells.
Figure 4:
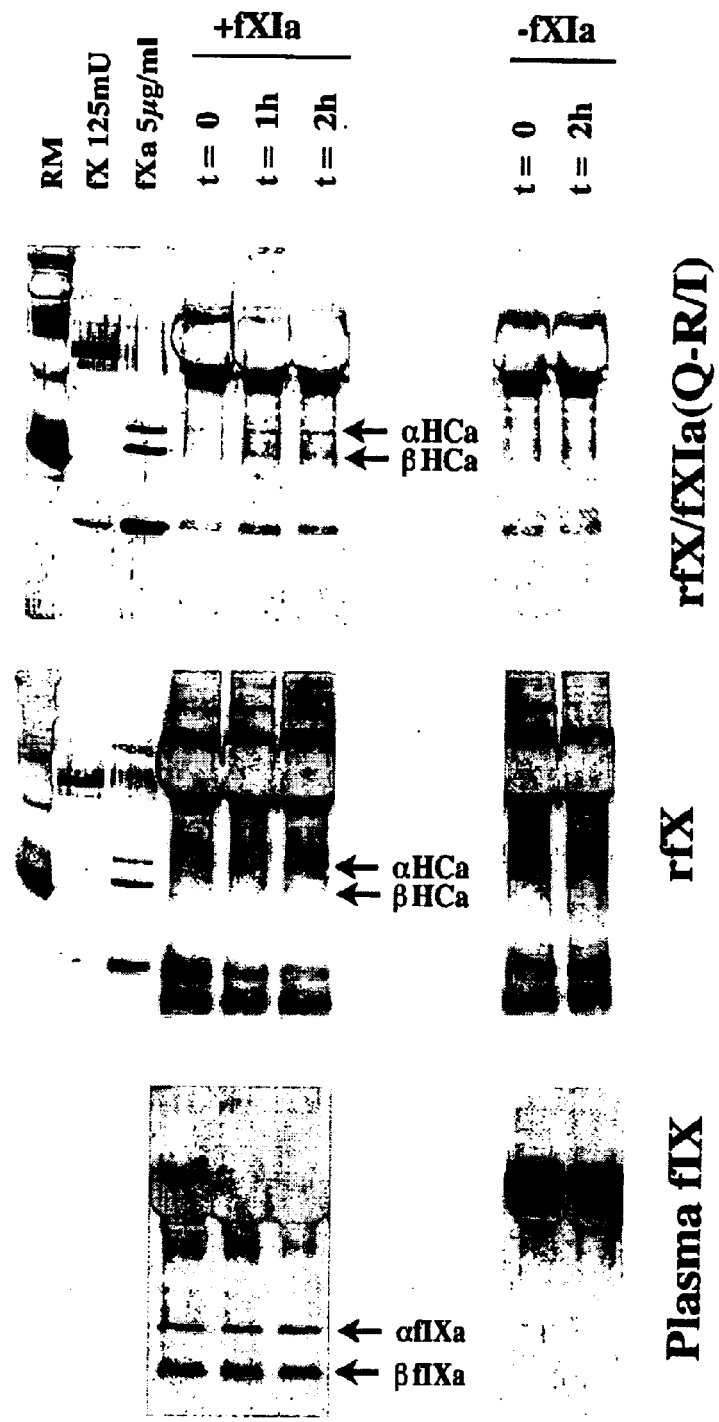
FIG. 4 shows a Western blot analysis after the in vitro activation of the factor X analog with factor XIa.

The present invention provides a Factor X analog with a modification in the region of amino-acid residues 226–235 with reference to the sequence shown in FIGS. 1A and 1B.

Herein, the term "modification" refers to a mutation, a deletion, an insertion, or a substitution of an amino acid residue within the designated sequence. The term "substitution" refers to replacement of an amino acid residue with a different amino acid residue within the polypeptide. The term "deletion" refers to the absence of at least one of the amino acid residues within the polypeptide, without replacement by another amino acid residue. The term "insertion" refers to the placement of an extra amino acid residue within the polypeptide. The term "mutation" refers to any change in the sequence of the designated polynucleotide or polypeptide, which change could be a deletion, an insertion, or a substitution of one or more nucleic acids or amino acids within the designated nucleic acid or amino acid sequence. Preferably, in the present invention, the modification is a substitution of at least one amino acid.

The amino acid modification in this region creates a new recognition and processing site for factor XIa or a derivative thereof, which site does not naturally occur in this position in the polypeptide. Factor XIa or a derivative thereof does not normally cleave Fx in the region of Glu-Arg-Gly-Asp-Asn-Asp-Phe-Thr-Arg/Ile (SEQ ID NO:10) of amino acids 226–234. Surprisingly, the factor X analog according to the present invention has an at least 2-fold, preferably an at least 5-fold, and especially an at least 10-fold increased ability to be activated by factor XIa compared to the factor X analog according to WO 98/38317.

In addition, it was a surprise to discover that the factor X analog according to the present invention at an antigen concentration of 4–8 μg/mL is able to reduce the coagulation time of factor IX- or FVIII-deficient plasma more effectively than >200 mU, preferably >500 mU, especially >1000 mU of plasma factor IX or FVIII.

Preferably, a minimum of one of the amino acid 226–230, especially 226–228, is modified. It is to be especially preferred if as many of the amino acids in the 226–235 domain as possible were to correspond to a cleavage site for factor XIa or a derivative thereof. According to the present invention, the introduction of a specific factor XIa cleavage sequence which comprises a minimum of 4, preferably a minimum of 6 amino acids, has proven to be especially useful.

The modification is preferably selected to ensure that the processing by means of factor XIa leads to a polypeptide which corresponds to the native factor Xa and which essentially resembles the naturally occurring factor Xa sequence and also has factor Xa activity.

To ensure optimum processing, in some cases, it may be necessary to modify the amino acid Ile235. Preferably, however, the $NH_2$-terminal amino acid isoleucine of the heavy chain should be maintained after the activation since this amino acid plays an important role in the formation of the substrate-binding pocket (Watzke et al.(1995), Molecular Basis of Thrombosis and Hemostasis, eds. Katherine High and Harold Roberts). Compared to the native factor X sequence, the factor X analogs according to the present invention are structurally different, in particular on the amino acid level, but their ability to be activated is comparable to the naturally occurring factor X and, after activation, factor Xa activity.

The invention makes available factor X analogs which are modified in the activation peptide relative to the naturally occurring factor X sequence and which have a changed protease specificity. Amino acid modifications may take place in position Ile235 (R1), Arg234, Thr233 (R2), Leu 232 (R3), Asn231 (R4), Asn230 (R5), Asp229 (R6), Gly228 (R7), and Arg227 (R8), while Arg234, however, preferably remains unchanged.

The factor X analogs according to the present invention preferably have a factor X sequence with Glu226-R8-R7-R6-R5-R4-R3-R2-Arg234-R1, wherein
a) R1 is an amino acid selected from the group Ile, Val, or Ala;
b) R2 is an amino acid selected from the group Thr, Ser or Asn;
c) R3 is an amino acid selected from the group Phe, Leu, Arg, or Ile;
d) R4 is an amino acid selected from the group Asp, Lys, Thr, or Glu;
e) R5 is an amino acid selected from the group Asn, Ser, Lys, Met, Thr, or Asp;
f) R6 is an amino acid selected from the group Phe, Thr, Ser, Pro, Leu, or Ile;
g) R7 is an amino acid selected from the group Ser, Gln, Ile, Thr, Asn, or Pro; and
h) R8 is an amino acid selected from the group Gin, Ser, His, Tyr, or Glu.

According to the present invention, preferably at least 4 amino acids of amino acids 226–234 differ from the natural factor X sequence, and preferably at least 3 of the amino acid modifications follow one immediately after the other.

Preferably, the amino acid sequences are of the kind that correspond to the amino acid sequences of the activation peptide of factor IX. These sequences can correspond to human, but also to animal (e.g., murine, porcine, etc.) factor IX activation peptide regions.

Embodiments of the factor X analogs according to the present invention to be preferred are FX analogs which are modified as follows:

a) R1=Val, R2=Thr, R3=Leu, R4=Asp, R5=Asn, R6=Asp, R7=Ser, and R8=Gln (SEQ ID NO:11) and which are processed by means of factor XIa or a derivative thereof;

b) R1=Ile, R2=Thr, R3=Leu, R4=Asp, R5=Asn, R6=Asp, R7=Ser, and R8=Gln (SEQ ID NO:12) and which are processed by means of factor XIa or a derivative thereof (FIG. 2);

c) R1=Val, R2=Thr, R3=Leu, R4=Lys, R5=Ser, R6=Thr, R7=GIn, and R8=Ser (SEQ ID NO:13) and which are processed by means of factor Ma or a derivative thereof; and d) R1=Ile, R2=Thr, T3=Leu, R4=Lys, R5=Ser, R6=Thr, R7=Gln, and R8=Ser (SEQ ID NO:14) and which are processed by means of factor XIa or a derivative thereof.

Other useful embodiments can be obtained by exchanging one or two other amino acids of molecules a)–d) above for which the assays made available according to the present invention have shown that they are cleavable by means of factor XIa.

The modifications can be carried out, for example, by site-specific in vitro mutagenesis or by PCR or by any other genetic engineering methods known in prior art which are suitable for specifically changing a DNA sequence in order to carry out specific amino acid exchanges.

According to the present invention, the activation of the factor X analog according to the present invention to form a native factor Xa or a factor Xa analog is carried out by means of factor XIa or a derivative thereof.

One of the difficulties encountered in the production of active factor Xa is its instability since in addition to factor Xaα, factor Xaβ and other intermediates, some possibly inactive, are formed as a result of autocatalysis.

To produce substantially intact active factor X/Xa and/or factor X/Xa-like molecules, it would therefore be desirable to obtain only proteins which lead to stable final products.

It is known that a preferred cleavage site for processing factor Xaα (FXaα) to form factor Xaβ (FXAβ) is located between Arg469 and Gly470. According to studies by Eby et al. (Blood, Vol. 80, Suppl. 1 (1992), p. 1214), in addition to a prominent carboxy-terminal peptide (amino acid residues 476–487) of factor X, an additional shorter peptide (amino acid residues 474 to 477) is found, which forms as a result of autocatalysis of factor Xaα. To focus on the specific processing of intact factor X to form active factor Xa, without obtaining inactive processing intermediates, the factor X analogs according to the present invention have other modifications.

Thus, according to a special embodiment of this invention, the factor X analog according to the present invention is further modified in the C-terminal region of the factor X amino acid sequence.

According to one embodiment of the present invention, a factor X analog of the type described above has an intact β-peptide (FXα). Herein, the term "β-peptide" refers to a 4 kD glycopeptide as known from prior art. The first cleavage site for the removal of the β-peptide by plasmin is located at Arg 469 according to amino acid sequence of FIG. 1, resulting in the removal of the complete C-terminus, i.e. the β-peptide (Pryzdial E. and Kessler G., J. Biol. Chem., 1996, pp. 16614–16620). In particular, the factor X analog according to the present invention has a modification in the region of the C-terminal β-peptide cleavage site which ensures that a cleavage of the β-peptide from factor X is prevented after factor X has been activated to form factor Xa. This results in a factor Xa molecule, of which up to 100% can be isolated in the form of an intact factor Xaα molecule.

The modification can be a mutation, deletion, or insertion in the region of the factor X amino acid sequence between amino acid positions Arg469 and Ser476 and potentially of Lys370. An amino acid modification to be preferred, however, is one in which it is not possible for a folding of the polypeptide, which would influence the structure and thus possibly the function and activity of the protein, to occur as a result of the amino acid exchange.

According to another embodiment of the present invention, the factor X analogs according to this invention comprise an exchange of one of the amino acid in position Arg469 and/or Gly470, with Arg469 preferably being exchanged for Lys, His, or Ile and with Gly470 preferably being exchanged for Ser, Ala, Val or Thr.

In addition to a mutation in position Arg469 and/or Gly470, the factor X analogs according to the present invention may have an additional mutation in position Lys370 and/or Lys475 and/or Ser476.

As a result of an amino acid modification in one of these positions, processing of factor Xaα into factor Xaβ or factor Xaγ is avoided since the naturally occurring processing sequence(s) is (are) modified to ensure that it is no longer possible for a potential autocatalytic cleavage of the carboxy-terminal peptide to occur.

According to yet another embodiment of the present invention, the factor X analog according to the present invention has a deletion of the carboxy-terminal β-peptide (FXB). Such a factor X analog can be produced by expressing a cDNA which codes for a factor X analog in a recombinant expression system, with only those sequences being cloned which code for the amino acids Met1 to Arg469.

In yet another embodiment of the present invention, the factor X analog according to this invention has a translation stop signal in the C-terminal region of the factor X sequence. This translation stop signal is preferably in a position which follows a C-terminal amino acid that is formed after natural processing. The translation stop signal is therefore preferably in the position of amino acid 470 of the factor X sequence so that the terminal Arg469 of factor Xaβ is maintained. To ensure this, codon GGC which codes for the amino acid Gly470 is exchanged for TAA, TAG, or TGA.

Another feature of the present invention relates to factor X analogs which are activated by treating them in vivo and in vitro with factor XIa or a derivative thereof to obtain native factor Xa or a factor Xa analog, i.e., the activated factor X analogs. Depending on the factor X analog that is used and activated, one obtains a polypeptide which corresponds to and is essentially identical to the native factor Xa or a polypeptide which, although it has factor Xa activity, has modifications relative to the native factor Xa sequence which, however, do not impair the biological activity. When the factor X analogs according to the present invention, which are modified in the region of the activation peptide in the sequence of the activation peptide, are activated, only polypeptides which correspond to the native factor Xa molecule are obtained. If such a factor X analog also has an additional translation stop signal in the C-terminal region of the β-peptide, molecules homologous to factor Xaβ are obtained. If, on the other hand, a factor X analog is used, which has a modification or modifications within the β-peptide sequence which has or have the effect that that β-peptide is not cleaved off, a factor Xaα analog with an amino acid exchange in the C-terminus of the molecule is obtained.

The factor X analogs according to the present invention have only modifications which change the specificity for the activation ability and which do not have a negative effect on the activity. Therefore, in all cases, biologically and functionally active factor Xa molecules and factor Xa analogs are obtained.

The activation in vivo and in vitro can be carried out by means of factor XIa or a derivative thereof. In this context, a factor XIa derivative can be a polypeptide or protein derived from factor XIa which differs from the native factor XIa, for example, with respect to its length (e.g., truncated forms) or which has been obtained by amino acid modification. In all cases, it is important to ensure that the factor XIa derivative also has the specific protease activity that is characteristic for factor XIa.

According to a special embodiment the present invention makes available factor X analogs which are preferably present in purified form as single-chain molecules. The single-chain factor X molecule is marked by a high stability and molecular integrity. Up to now, it had not been possible to isolate a single-chain factor X molecule in purified form since it is very rapidly processed into the double-chain form (Fair et al., Blood 64 (1984), pp. 194–204). The recombinant single-chain factor X analogs can be processed by specific processing to form the double-chain factor X form and can be subsequently activated into factor Xa or the factor Xa analog. This can be accomplished by having the single-chain factor X analog come into contact with furin, by processing it, and by subsequently activating it by means of factor XIa or a derivative thereof.

The double-chain factor X analog can be activated to form factor Xa or a factor Xa analog. This can be accomplished, for example, by using a factor X analog which, as a result of the mdification according to the present invention in the region of the activation peptide, has a factor XIa cleavage site, which is expressed and isolated in a recombinant cell as a single-chain molecule, and which is subsequently processed by bringing it into contact with furin and then cleaved by means of factor XIa or a derivative thereof to form an activated factor Xa molecule.

A factor X analog which was isolated as a double-chain molecule from a cell culture can be treated directly with factor XIa or a derivative thereof.

Due to the selective and site-specific processing reaction, a factor Xa or a factor Xa analog obtained in this manner has a high stability and structural integrity and, in particular, is free from inactive factor X/Xa analog intermediates and autoproteolytic degradation products. In addition, the factor X analog according to the present invention can be especially readily activated by means of factor XIa or a derivative thereof, with the ability to be activated being at least 2-fold, preferably at least 5-fold, and especially at least 10-fold increased when compared to the factor X analogs described in WO 98/38317. Surprisingly, it was discovered that the constructs according to the present invention can be more readily activated as a result of the fact that a minimum of 4, preferably a minimum of 6 of amino acid 226–235 are amino acids that differ from those in the natural factor X molecule and that preferably at least 3 of the exchanged amino acid follow one immediately after the other.

An additional feature of the present invention relates to the recombinant DNA which codes for the factor X analogs according to the present invention. After its expression, the recombinant DNA results in a suitable host cell in a factor X analog with an amino acid sequence that corresponds to human factor X, except that it has an amino acid modification that influences the processing specificity and the processing products. The biological coagulation activity, however, is not in any way negatively influenced; instead, surprisingly, frequently even an increase in the activity results.

According to yet another feature of the present invention, transformed cells containing the recombinant DNA are also made available.

An additional feature of the present invention relates to a preparation containing a purified factor X analog or a precursor protein thereof which has the amino acid modification according to this invention in the region of the naturally occurring factor Xa activation site. The modification in the region of the activation cleavage site is a new recognition and processing cleavage site—which does not naturally occur in this position in the polypeptide—for factor XIa or a derivative thereof which does not normally process the polypeptide in this position. The preparation can be a purified preparation of factor X analogs, with the polypeptides being obtained from a cell culture system either after isolation from the supernatant of the cell culture or from an extract of a cell culture. A prepurified recombinant factor X analog from a cell culture system can be further purified using procedures known from prior art. In this context, chromatographic processes, such as gel filtration, ion-exchange or affinity chromatography, are particularly suitable for use.

According to one embodiment of the invention, the preparation according to this invention preferably contains the factor X analog as a single-chain molecule in isolated form. Such a preparation is produced by isolating a factor X analog, which was obtained by recombinant production, as a single-chain molecule from a cell system, preferably from a cell culture of cells deficient in endoprotease.

A special feature of the present invention relates to the fact that the preparation contains a single-chain factor X analog with a modification which, after processing by means of furin, allows an in vitro activation into factor Xa by means of factor XIa or a derivative thereof. The activation is accomplished by bringing the factor X analog into contact with the proteases, which leads to a cleavage into the mature factor X form and, as a result of the modification, to a cleavage of the activation peptide and to the formation of factor Xa and the factor Xa analog.

In the preparation according to the present invention, the factor X analog can be present either as factor $X\alpha$ ($FX\alpha$) or with a deletion of the $\beta$-peptide.

The preparation contains, in particular, a factor X analog in an enzymatically inactive form with a purity of a minimum of 80%, preferably 90%, and especially 95% and does not contain any inactive proteolytic intermediates of the factor X/Xa analog.

According to another embodiment of the present invention, the preparation according to this invention preferably contains the factor X analog as a double-chain molecule in isolated form. To accomplish this, for example, a factor X analog which has been obtained by means of recombinant production as a single-chain molecule from a cell system is cleaved in vitro, i.e., outside the cell, by means of furin to obtain the double-chain form. This can be accomplished by mixing the protease directly with the supernatant of the culture of the clones that express the factor X analog, either by mixing the purified protease or a cell culture supernatant of a cell culture which expresses the protease in recombinant form or by means of co-cultivation of factor X analog- and protease-expressing clones.

According to a special embodiment of the present invention, the preparation containing the purified, single-chain or double-chain factor X analog contains a physiologically acceptable matrix and is potentially formulated as a pharmaceutical preparation. The preparation can be formulated using substantially known prior art methods, it can be mixed with a buffer containing salts, such as NaCl, $CaCl_2$, and amino acids, such as glycine and/or lysine, in a pH range from 6 to 8, and it can be formulated as a pharmaceutical preparation. Until needed, the purified preparation containing the factor X analog can be stored in the form of a finished solution or in lyophilized or deep-frozen form. Preferably the preparation is stored in lyophilized form and is dissolved into a visually clear solution using an appropriate reconstitution solution.

But the preparation according to the present invention can also be made available as a liquid preparation or as a liquid that is deep-frozen.

The preparation according to the present invention is especially stable, i.e., it can be allowed to stand in dissolved form for a prolonged time prior to application. It was found that the preparation according to this invention can be allowed to stand for several hours and even days without loss of activity.

The preparation according to the present invention can be placed into a suitable device, preferably an application device, in combination with factor XIa or a derivative thereof.

The preparation according to the present invention which contains a factor X analog in combination with factor XIa or a derivative thereof which is able to activate the factor X analog into factor Xa or the factor Xa analog can be made available in the form of a combination preparation comprising a container that holds factor XIa which is immobilized on a matrix, potentially in the form of a miniature column or a syringe complemented with a protease, and a container containing the pharmaceutical preparation with the factor X analog. To activate the factor X analog, the factor X analog-containing solution, for example, can be pressed over the immobilized protease. During storage of the preparation, the factor X analog-containing solution is preferably spatially separated from the protease. The preparation according to the present invention can be stored in the same container as the protease, but the components are spatially separated by an impermeable partition which can be easily removed before administration of the preparation. The solutions can also be stored in separate containers and be brought into contact with each other only shortly prior to administration.

The factor X analog can be activated into factor Xa shortly before immediate use, i.e., prior to the administration to the patient The activation can be carried out by bringing a factor X analog into contact with an immobilized protease or by mixing solutions containing a protease, on the one hand, and the factor X analog, on the other hand. Thus, it is possible to separately maintain the two components in solution and to mix them by means of a suitable infusion device in which the components come into contact with each other as they pass through the device and thereby to cause an activation into factor Xa or into the factor Xa analog. The patient thus receives a mixture of factor Xa and, in addition, a serine protease which is responsible for the activation. In this context, it is especially important to pay close attention to the dosage since the additional administration of a serine protease also activates endogenous factor X, which may shorten the coagulation time.

According to a useful embodiment of the invention, the pharmaceutical preparation is made available in a suitable device, preferably an application device, either in the form of a frozen liquid or in freeze-dried form. A suitable application device, for example, is a double-compartment syringe of the type described in the AT 366 916 or AT 382 783.

One especially useful feature of this invention is that the preparation can contain a factor X analog with a modification which makes possible an in vivo activation of the factor X analog into factor Xa. In particular, the factor X analogs of the preparation according to the present invention have a modification which represents a recognition and cleavage site for factor XIa or a derivative thereof, thus making it possible for them to be cleaved by this protease in vivo to form native factor Xa or the factor Xa analog. As a result, the preparation according to the present invention can be used to arrest bleeding both in patients with deficiencies of factor IX and factor VIII and in patients with factor VIII inhibitor.

The preparation according to the present invention can be made available as a pharmaceutical preparation with factor Xa activity in the form of a one-component preparation or in combination with other factors in the form of a multi-component preparation.

Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, preferably using a method, such as is described in EP 0 714 987.

Since any biological material can be contaminated with infectious microorganisms, the preparation may have to be especially treated to inactivate or deplete viruses in order to ensure that a safe preparation is obtained.

Another feature of this invention relates to making available a preparation which contains a factor Xa analog with a high stability and structural integrity and which, in particular, is free from inactive factor X/Xa analog intermediates and autoproteolytic degradation products and which can be produced by activating a factor X analog of the type described above and by formulating it into an appropriate preparation.

An additional feature of the present invention relates to the use of a preparation of the type described above to produce a drug. A drug which contains a factor X analog and/or a factor Xa analog according to the present invention is suitable especially for the treatment of patients with blood coagulation disorders, such as patients suffering from hemophilia or hemophiliacs with inhibitory antibodies, and, in particular, as a preparation with factor VIII inhibitor bypass activity.

Another feature of this invention relates to the use of a nucleic acid which contains the coding sequences of the factor X analog according to this invention for the production of a drug. In this context, the nucleic acid, to the extent that it contains suitable expression control sequences, can be administered in the form of naked nucleic acid, it can be integrated into a recombinant expression vector, or it can be bound to a matrix, such as either a phospholipid or a viral particle. The nucleic acid can be used to manufacture a drug which is especially suitable for use in the treatment of patients with blood coagulation disorders, such as hemophilia patients or hemophiliacs with inhibitory antibodies. Another potential application is the use of the nucleic acid in gene therapy.

Another feature of the present invention relates to a process for the production of the factor X analogs according to this invention and a preparation containing a factor X analog according to this invention. To accomplish this, a sequence coding for a factor X analog is introduced into a suitable expression system and the relevant cells, preferably permanent cell lines, are transfixed with the recombinant DNA. The cells are cultivated under optimum conditions for gene expression, and factor X analogs are either isolated from the extract of a cell culture or from the supernatant of the cell culture. The purification of the recombinant molecule can be further carried out using all conventionally known chromatographic procedures, such as anion- or cation-exchange chromatography, affinity or immunoaffinity chromatography or a combination thereof.

To produce the factor X analogs according to the present invention, the complete cDNA coding for factor X is cloned into an expression vector. This is carried out by means of the generally known cloning techniques. The nucleotide sequence coding for factor X is subsequently modified to ensure that the coding sequence in the region of the activation peptide and possibly in the region of the C-terminal β-peptide is changed to ensure that a factor X molecule of the type described above can be produced. To accomplish this, genetic engineering methods known from prior art are used, for example, site-specific in vitro mutagenesis, or deletion of sequences, for example, by means of digestion through restriction by endonucleases and insertion of different, changed sequences, or by PCR. The factor mutants thus produced are then inserted into an expression system suitable for the recombinant expression and are subsequently expressed.

The factor X analogs according to the present invention can also be produced by means of chemical synthesis.

The factor X analogs are preferably produced by means of recombinant expression. The production by means of genetic engineering methods can be carried out with all known expression systems, e.g., permanent cell lines or viral expression systems. The permanent cell lines are produced by stable integration of exogenous DNA into the host cell chromosome, e.g., of Vero, MRC5, CHO, BHK, 293, Sk-Hep1, especially liver and kidney cells, or by an episomal vector derived, e.g., from papillomavirus. Viral expression systems, such as vaccinia virus, baculovirus, or retroviral systems can also be used. The cell lines normally used are Vero, MRC5, CHO, BHK, 293, Sk-Hep1, glandular, liver, and kidney cells. Eukaryotic expression systems to be used include yeasts, endogenous glands (e.g., glands of transgenic animals) and other cell types. It is, of course, also possible to use transgenic animals to express the polypeptides according to the present invention or derivatives thereof. To express the recombinant proteins, especially CHO-DHFR cells have been shown to be useful (Urlaub et al., Proc. Natl. Acad. Sci. USA 77, (1980), pp. 4216–4220).

For the recombinant production of the factor X analogs according to the present invention, it is also possible to use prokaryotic expression systems. Especially suitable are systems which allow an expression in E. colior B. subtilis.

The factor X analogs are expressed in the appropriate expression systems using a suitable promoter. For the expression in eukaryotes, all known promoters, such as SV40, CMV, RSV, HSV, EBV, β-actin, hGH, or inducible promoters, such as lssp or metallothionein promoter, can be used. The factor X analogs are preferably expressed using the β-actin promoter in CHO-DHFR cells.

According to one embodiment of the invention, the method for producing the preparation according to the present invention comprises the following steps: preparing a DNA which codes for a factor X analog, transformation of a cell with the recombinant DNA, expression of the factor X analog, potentially in the presence of a protease, isolation of the factor X analog, and potential purification by means of a chromatographic procedure.

According to one embodiment of the method, the factor X analog is isolated as a double-chain molecule.

For this purpose, the factor X analog is expressed in a cell which allows processing of profactor X analogs in double-chain factor X analogs.

The double-chain factor X analog thus obtained can subsequently be isolated, purified, and, as described above, stably stored until further use.

According to one embodiment of this invention, the activation is triggered by a chromatographic step in which the protease is immobilized on a matrix. Purified double-chain factor X analog is passed over a matrix to which the protease is bound, and from the eluate, purified factor Xa is isolated.

According to another embodiment of the invention, the components are mixed and the protease is selectively removed from the mixture.

In addition, it is, of course, also possible to process a single-chain profactor X analog into the double-chain factor X analog form and activate it into factor Xa in a single process.

The reaction conditions of processing reaction(s) and the activation can be readily optimized by those skilled in the art depending on the experimental setup of any given situation. In this context, it should be noted that the flow rate of the reaction participants used is of special importance to the length of contact time. This flow rate should be in a range from 0.01 ml/min to 1 mL/min. Other important parameters are the temperature, the pH value, and the elution conditions. At the end of the flow time, the activated factor Xa can optionally be further purified by means of selective chromatography. Carrying out the method with protease that is bound to a matrix offers a special advantage since, as a result of the use of a matrix, preferably of chromatographic columns, the reaction setup makes it possible to include an additional purification step.

An additional feature of the production of a factor X analog according to this invention is that the factor X analog is isolated as a single-chain molecule. For this purpose, the factor X analog is expressed in a cell in which the cleavage of the light and heavy chain of factor X and/or a factor X analog cannot take place. Furin is of the important proteases that are responsible for the cleavage of factor X into a light and a heavy chain. From such an endoprotease-deficient mutant cell, it is possible to isolate the factor X analog in the form of a single-chain molecule. A factor X analog that was isolated in this manner and potentially also purified is subsequently brought into contact with furin under conditions under which the single-chain factor X analog is cleaved into the double-chain factor X form. Factor X analogs according to the present invention which have a modification in the region of the activation peptide that makes a cleavage by factor XIa possible can subsequently be activated by this method, possibly directly by bringing them into contact with factor XIa or a derivative thereof, to form factor Xa or the factor Xa analog.

According to another feature of this invention, using the method according to the invention, a preparation containing the active factor Xa or an active factor Xa analog is obtained by subjecting a factor X analog that had been obtained as described above to an activation step and by processing the activated polypeptide into a purified preparation which is potentially formulated as a pharmaceutical compound.

Using the factor X analogs according to the invention which are activated by a process described above into factor Xa, a purified factor Xa and/or factor Xa analog with a high stability and structural integrity is obtained which, in particular, is free from inactive factor X/Xa intermediates.

This invention will be explained in greater detail on the basis of the following examples and figures shown in the drawing, without, however, thereby limiting the invention in any way.

EXAMPLES

Example 1

Construction and Expression of recombinant Factor X Wild Type (rFX) and Factor X/FXIa (Q-R/I) Analogs a. Production of the rFX expression vector phAct-rFX The cDNA of FX was isolated from a human liver lambda-cDNA bank as described by Messier et al. (Gene 99 (1991), pp. 291–294). By means of PCR, using oligonucleotide #2911 (5'-ATTACTCGAGAAGCTTACCATGGGGCGCCCACTG-3') (SEQ ID NO:3) as the 5' primer and oligonucleotide #2912 (5'-ATTACAATTGCTGCAGGGATCCAC-3) (SEQ ID NO:4) as the 3' primer, a DNA fragment was amplified from a positive clone, which DNA fragment contains the 1,457 kB FX-coding sequence and 39 bp of the 3' nontranslated region, flanked by an XhoI cutting site on the 5' end and an MfeI cutting site on the 3' end. In addition, by means of primer #2911, the sequence ACC was inserted in front of ATG of FX, thus ensuring that an optimum Kozak translation initiation sequence forms. Subsequently this PCR fragment was cloned as XhoI/MfeI fragment into the expression vector phAct which had been cut with SalI an EcoRI. The expression factor phAct comprises approximately 3.3 kb of the promoter, 78 bp of 5' UTR, and the approximately 1 kb measuring intron of the human beta-actin gene (Fischer et al., FEBS Lett. 351 (1994), pp. 345–348), a multiple cloning cutting site and the SV40 polyadenylation site. The resulting expression plasmid was called phAct-rFX.

b. Production of the phAct-rFX/FXIa (Q-R/I) expression plasmid

To produce recombinant FX/FXIa (Q-R/I) analogs, the amino acid sequence from position 227 to 234 (Arg-Gly-Asp-Asn-Asn-Leu-Thr-Arg/Ile; SEQ ID NO:15) which serves to activate FX into FXa was replaced with the intrinsic tenase complex FIXa/FVIIIa or by the extrinsic FVIIa/TF complex, by the sequence Gln-Ser-Phe-Asn-Asp-Phe-Thr-Arg/Ile (hereinafter referred to as (Q-R/I)), specifically activated by means of the coagulation factor XIa (FIG. 2). Q-R was prepared in conformity with the second FXIa cutting site, such as it is present in the 'natural' substrate FIX. The expression plasmid for this rFX analog is derived from plasmid phAct/rFX. For cloning purposes, the HindIII-NaeI DNA fragment from the phAct-rFX expression plasmid which comprises the FX-coding region from position +1 to +1116 was inserted into the HindIII-SmaI restriction cutting sites of plasmid pUC19. The resulting plasmid was called pUC/FX. This made it possible for the FX sequence of nucleotide 508 to 705 which corresponds to amino acids 160 to 235 to be removed from the pUC/FX plasmid via Bsp120I and BstXI restriction cuts and to be replaced by a mutated FX-DNA fragment. The mutated DNA fragment contains the FX-exogenic cleavage site for FXIa, instead of the FIXa/FVIIIa and FVIIa/TF site, and is produced by means of PCR. Plasmid phAct/rFX serves as a model for the PCR. To produce the Gln-Ser-Phe-Asn-Asp-Phe-Thr-Arg/Ile (SEQ ID NO:16) (Q-R/I) cleavage site, oligonucleotide #4211 (5'-GGCAAGGCCTGCATTCCCACA-3') (SEQ ID NO:5) is used as the 5' primer and oligonucleotide #5039 (5'-GCGCTCCCACGATCCTGGTGAAGTCATTAA-AGCTTTGCTCAGGCTGCGTCTGGTT-3') (SEQ ID NO:6) is used as the 3' primer. Therefore, amino acids Arg, Gly, Asp, Asn, and Leu are replaced in positions 227, 228, 229, 231, and 232 with Gln, Ser, Phe, Asp, and Phe. The PCR product is recut with Bsp 120I and BstXI and inserted into the pUC-FX plasmid that had been opened with Bsp120I/BstXI. Subsequently, the DNA fragment which contains the new cleavage site is reinserted via HindIII/AgeI into phact-FX which had been cut with the same restriction enzymes. The resulting plasmid is called phAct-FX/FXIa (Q-R/I).

c. Expression of rFX and of the rFX/FXIa (Q-R/I) analog in CHO cells

To establish stable rFX/FXIa-expressing cell lines, the expression plasmid phAct-rFX and phAct-rFX/FXa (Q-R/I) is co-transfixed with the selection marker pSV-dhfr in the dhfr-deficient CHO cells (Fischer et al., FEBs Lett. 351 (1994), pp. 345–348). For all other expression and function analyses, the cell cultures are incubated after a complete media change with a serum-free selection medium in the presence of 10 $\mu$g/mL vitamin K for 24 h. The expression of rFX in the resulting cell clones is demonstrated on the basis of the quantity of antigen (ELISA, Asserachrom, Boehringer Mannheim), and the recombinant protein is subsequently characterized with SDS-PAFW (FIG. 3). As can be seen in the Western blot as well, both the rFX wild type and the rFX/FXIa (Q-R/I) molecules are present in the form of a light chain (LC) of approximately 22 kD and a heavy chain (HC) of approximately 50 kD which correspond to the plasmatic factor X forms. In addition, a 75 kD protein band can be seen. The 75 kD protein corresponds to the single-chain (SC) FX molecule, the presence of which had already been described in the supernatants of FX-transfixed CHO cells (Wolf et al., J. Biol. Chem. 266 (1991), pp. 13729–13730) and in human plasma (Fair et al., Blood 64 (1984), pp. 194–204).

Example 2

In-Vitro Activation of the rFX/FXIa (Q-R/I) Molecules by means of Factor XIa

To demonstrate the cleavability of the newly inserted activation sites by means of factor XIa, the supernatants of the cell culture are mixed with purified factor XIa in the presence of 5 mM $CaCl_2$. Aliquot portions of the reaction batches are tested for cleavage both prior to the incubation and after different incubation times at 37° C. by means of the Western blot analysis (FIG. 4). The identification of the rFX molecules is carried out by means of a polyclonal anti-human FX antibody. The positive control used is purified plasma factor IX (Stago) which is the natural substrate for FXIa. To work under uniform conditions, FIX is diluted prior to use in supernatants of the cell culture of nontransfixed CHO cells. The conversion of FIX into the activated forms (FIXa and FIXb) shows that FXIa is able to cleave its homologous cutting site in FIX in supernatants of the cell culture. The reaction batch with rFX wild type serves as a negative control since this molecule does not contain any FXIa cleavage site and should therefore not be specifically recognized and cleaved by FXIa. As expected, compared to rFX in the absence of FXIa, no change for rFX is visible in the protein pattern after incubation with FXIa.

In contrast, after an incubation time of 1 h at 37° C. in the presence of $CaCl_2$, the reaction batch of FXIa, with rFX/FXIa (Q-R/I) as a substrate, shows protein bands of approximately 36 kD and 32 kD which resemble the activated alpha and beta forms (aHCa and bHCa) of the heavy chain of FX. In the absence of FXIa, these cleaved molecules are not present. The presence of a form which is similar to bHCa and which forms as a result of the autocatalytic cleavage of C-terminal amino acids of the heavy chain of aHCa points to the functionality of the generated activated rFXa molecules. These results show that by replacing the naturally existing activation sequence in FX with an activation cleavage site for FXIa, it is possible to generate rFX analog molecules which can be activated by FXIa and which can subsequently be converted into molecules that resemble FXa.

The method described can be used to test all other factor X analogs for the properties according to the present invention.

Example 3 a. Activity of the rFX/FXIa (Q-R/I) Analog compared to rFX Wild Type in FIX-Deficient Plasma To test the functionality of the rFX analog, FIX-deficient plasma is mixed with the supernatant of the CHO-rFX/FXIa (Q-R/I) cell culture, and the coagulation time cascade is measured after the intrinsic coagulation cascade has been activated (Table 1). For this purpose, 50 $\mu$L of the supernatant which was partially concentrated by ultrafiltration, 50 $\mu$L of FIX-deficient plasma, and 50 $\mu$L of DAPPTIN (Baxter AG) were mixed. After an incubation time of 4 min at 37° C., the reaction is initiated with 50 $\mu$L of 25 mM $CaCl_2$ which had been preheated to 37° C. The coagulation time is measured in the coagulometer (Amelung, KC10A). The activity in mU FIX is determined using a straight calibration line that is generated with plasmatic FIX. The coagulation times obtained with the rFX analogs are correspondingly given as mU FIX equivalents. Supernatants of the cell culture of rFX wild type-expressing CHO cells (CHO-rFX) and supernatants of the cell culture of nontransfected CHO cells (CHO neg.) serve as the control. To exclude nonspecific effects and to take into account experimental variations that are based on the conditions of the cell culture, 7 to 10 different cell culture surpernants of cells, which have the same growth stages and similar expression rates, were tested for each construct.

Supernatants of cell cultures of CHO-rFX and CHO neg. lead to coagulation times similar to those of the dilution buffer in which the standards and samples are diluted and are thus given as '<1.56' mU FIX equivalent (smallest evaluable value in the coagulation tests due to the straight calibration line).

Compared to the coagulation times that had been determined with 200 mU plasmatic FIX, however, the coagulation times for the supernatants of CHO-rFX/FXIa (Q-R/I) cells determined with concentrations of the analog in a range from 4.1 to 7.7 μg/mL were significantly shorter and are therefore given as '>200' mU FIX equivalent.

These results show that by replacing the 8 C-terminal amino acids of the FX activation peptide with the 8 C-terminal amino acids of the activation peptide of factor IX, an rFX analog molecule was generated which, after activation of the intrinsic coagulation cascade, leads to a significant coagulation of a factor IX-deficient plasma.

b. Determination of the functional activity of the rFX/FXIa (Q-R/T) analog in FIX- and FVIII-deficient plasmas after a pretreatment of the supernatants of the cell culture with serine protease inhibitors.

To be able to eliminate the possibility that the coagulation times obtained with the rFX/FXIa (Q-R/I) analogs are not the result of the presence of traces of already activated rFX molecules in the supernatants of the cell culture but are instead the result of the conversion of the rFX analogs into rFXa after the activation of the intrinsic coagulation cascade by DAPPTIN, prior to use, all supernatants are mixed with a serine protease inhibitor (1 mM Pefabloc, Boehringer Mannheim) which permanently inactivates activated serine proteases. Excess inhibitor which would inhibit the coagulation following DAPPTIN activation is subsequently removed by means of dialysis against Tris pH 7.4, NaCl 50 mM, Tween 0.01%. The supernatants thus treated are subsequently used in the coagulation test The serine protease inhibitor concentration was selected to ensure that the quantities of FXa which lead to a coagulation similar to that of the untreated rFX/FXIa (Q-R/I) cell culture supernatants were completely inhibited (Table 2). The results of this preliminary experiments show that an inhibitor concentration of 1 mM is able to completely inactivate FXa quantities which have considerably shorter coagulation times in FIX-deficient plasma than those obtained with the rFX/FXIa (Q-R/I) analogs (comparison with Table 1).

The functionality of the thus pretreated supernatants is measured both in the FIX and in the FVI coagulation test (Table 3). The FVIII coagulation test is carried out in the same way as the FIX coagulation test, except that instead of FIX-deficient plasma, FVIII-deficient plasma is used, that the incubation prior to the initiation with $CaCl_2$ lasts 3 min, and that the calibration curve is plotted with plasmatic FVIII.

Supernatants of CHO-rFX cells are below the limit of evaluation (1.56 mU) both in FIX- and in FVIII-deficient plasma. Similarly, CHO neg. supernatant does not lead to a shorter coagulation time even if this supernatant was treated with 1 mU FXa prior to the treatment with the inhibitor. These controls show that even if already preactivated FX would be inactivated by the inhibitor in the cell culture supernatant . . . , and that the coagulation is not mediated by potentially existing CHO-specific proteases.

The pretreated plasmatic FIX (FIX) in comparison with FIX that has not been pretreated (FIX without inhibitor and dialysis) has a lower coagulation activity in FIX-deficient plasma, which indicates that either a portion of the serine proteases, even in the unactivated form, is inhibited by the inhibitor or is lost as a result of the process (dialysis).

In spite of the pretreatment of the inhibitor, in FIX and in FVIH coagulation tests, no significant changes in the measured values are observed in the CHO-rFX/FXIa (Q-R/I) supernatants when compared to untreated supernatants. These experiments show that after activation of the intrinsic coagulation cascade, recombinant FX analog molecules which have a FIX activation cleavage site for FXIa lead to a significant coagulation of FIX and FVIII-deficient plasmas. In summary, it has been demonstrated that these recombinant FX/FXIa (Q-R/I) analog molecules have properties which indicate that the molecules may prove to be successful candidates for the production of therapeutic preparations which might be useful in the treatment of patients suffering from hemophilia or from hemophilia with inhibitory antibodies.

TABLE 1

Functional activity of the rFX/FXIa (Q-R/I) molecules in FIX-deficient plasma.

| Sample | Antigen μg\ml | mU FIX equivalent | Coagulation time in seconds |
|---|---|---|---|
| rFX/FXIa (Q-R/I) | | | |
| sup1 | 6.3 | >200 | 46.5 |
| sup2 | 4.4 | >200 | 47.7 |
| sup3 | 6.6 | >200 | 46.4 |
| sup4 | 4.8 | >200 | 43.2 |
| sup5 | 4.1 | >200 | 45.2 |
| sup6 | 6.4 | >200 | 43.1 |
| sup7 | 6.6 | >200 | 43.1 |
| sup8 | 4.3 | >200 | 45.2 |
| sup9 | 5.7 | >200 | 39.4 |
| sup10 | 7.7 | >200 | 44.2 |
| rFXwt | | | |
| sup1 | 2.1 | <1.56 | 107.8 |
| sup2 | 3.1 | <1.56 | 97.8 |
| sup3 | 1.6 | 3 | 84.7 |
| sup4 | 2.4 | <1.56 | 90.4 |
| sup5 | 3.2 | <1.56 | 92.4 |
| sup6 | 4.4 | <1.56 | 96.2 |
| sup7 | 6.7 | <1.56 | 92.7 |
| CHO neg. | | <1.56 | 179.7 |
| Plasma FIX | 1* | | 50.7 |
| Plasma FIX | 0.5* | | 54.5 |
| Plasma FIX | 0.125* | | 65.6 |
| Plasma FIX | 0.0625* | | 72.2 |
| Plasma FIX | 0.0078* | | 89.1 |
| Buffer | 0 | | 109.7 |

200, 100, 25, 12.5 and 1.56 mU plasmatic FIX were used. To convert these values into μg/mL, it was assumed that 1 unit FIX corresponds to approximately 5 μg of FIX/mL.

TABLE 2

Determination of the inactivation of FXa by means of a preliminary treatment with Pefabloc and subsequent dialysis in the FIX coagulation test

| Sample | mU used | Coagulation time in seconds | mU FIX equivalent |
|---|---|---|---|
| FXa | 5 | 19.9 | >200 |
| FXa | 1 | 32.5 | >200 |
| FXa | 0.5 | 45 | >200 |
| FXa | 0.1 | 76.1 | 10 |
| FXa + Inh | 5 | 93.4 | 1.94 |
| FXa + Inh | 1 | 115.9 | <1.56 |

TABLE 2-continued

Determination of the inactivation of FXa by means of a preliminary treatment with Pefabloc and subsequent dialysis in the FIX coagulation test

| Sample | mU used | Coagulation time in seconds | mU FIX equivalent |
| --- | --- | --- | --- |
| FXa + Inh | 0.5 | 113.5 | <1.56 |
| FXa + Inh | 0.1 | 115.3 | <1.56 |
| Plasma | 200 | 52.9 | |
| Plasma | 1.56 | 95.7 | |
| Buffer | | 114.7 | |

TABLE 3

Functional activity of CHO-rFX/FXIa (W-R/I) supernatants of a cell culture after a preliminary treatment with Pefabloc and dialysis in FIX- and FVIII-deficient coagulation tests.

| Sample | Antigen μg\ml | mU FIX equivalent | mU FVIII equivalent |
| --- | --- | --- | --- |
| rFX/FXIa (Q-R/I) | | | |
| sup1 | 6.3 | >200 | >200 |
| sup2 | 4.4 | 100 | >200 |
| sup3 | 6.6 | >200 | >200 |
| sup4 | 4.8 | 167 | >200 |
| sup5 | 4.1 | >200 | >200 |
| sup6 | 6.4 | >200 | >200 |
| sup7 | 6.6 | >200 | >200 |
| sup8 | 4.3 | >200 | >200 |
| sup9 | 5.7 | >200 | >200 |
| sup10 | 7.7 | >200 | >200 |
| rFXwt | | | |
| sup1 | 2.1 | <1.56 | <1.56 |
| sup2 | 3.1 | <1.56 | <1.56 |
| sup3 | 1.6 | <1.56 | <1.56 |
| sup4 | 2.4 | <1.56 | <1.56 |
| sup5 | 3.2 | <1.56 | <1.56 |
| sup6 | 4.4 | <1.56 | <1.56 |
| sup7 | 6.7 | <1.56 | <1.56 |
| CHO neg. | | <1.56 | <1.56 |
| CHO neg. + Fxa | | <1.56 | <1.56 |
| Plasma FIX (−Inh. −Dial.)* | 25 mU | 25 | |
| Plasma FIX | 25 mU | 4 | |
| Plasma FVIII (−Inh. −Dial.)* | 50 mU | | 48 |
| Plasma FVIII (−Inh. −Dial.)* | 3.125 mU | | 3 |

These samples were used in the tests without being treated (without the addition of serine protease inhibitor and dialysis).

Figure 5:
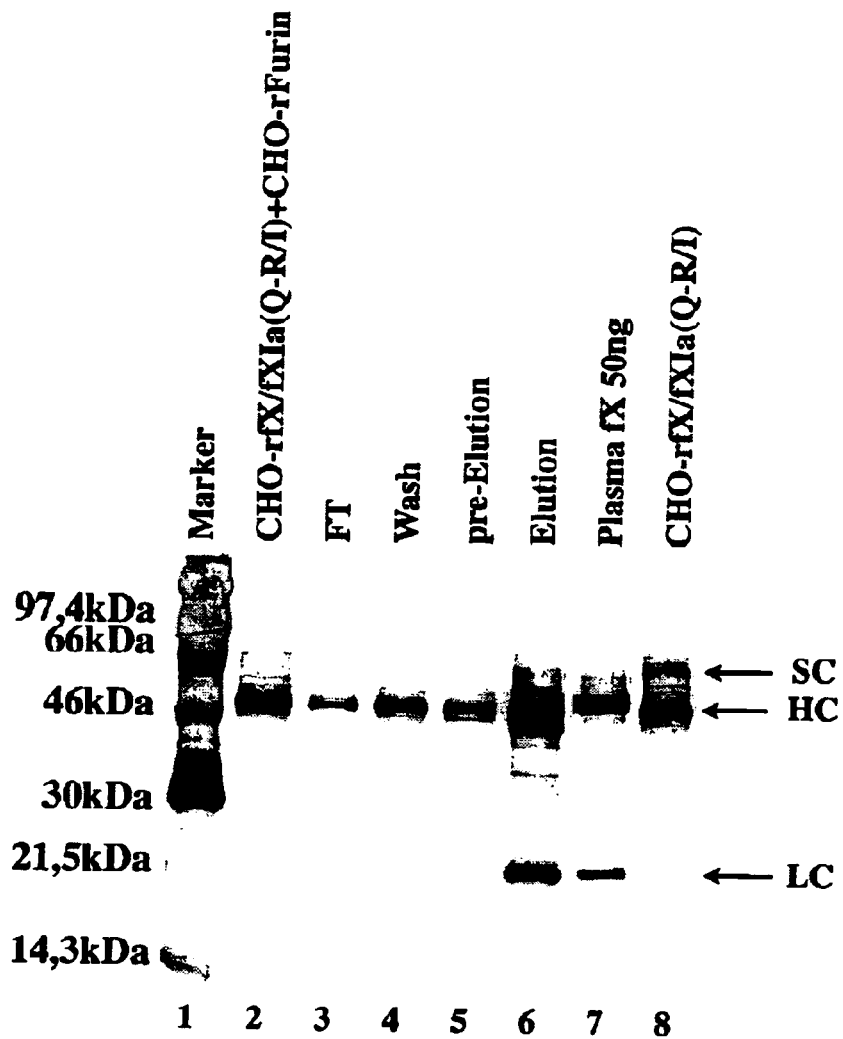
FIG. 5 shows the purification of rfX/rFXIa (Q-R/I) by anion exchange chromatography.

Example 4
Activity of Purified rfX/fXIa(Q-R/I) Molecules in Vitro and in Vivo rfX/fXIa(Q-R/I) molecules were purified from cell culture supernatants of stable CHO-rfX/fXIa(Q-R/I) cell clones (established as described in example 1.c) by anion exchange chromatography. Because of the presence of partially proteolytically incompletely matured precursor rfX molecules in the supernatant of recombinant cell lines used for purification (FIG. 5, lane 8), the supernatant was first pre-incubated for 4 hours at 37° C. with conditioned medium from CHO cell clones expressing a secreted form of the endoprotease furin. Furin is a serine protease which performs the conversion of fX single chain into heavy/light chain as well as the propeptide removal in vitro. By this treatment processing of immature fX molecules is completed in vitro (FIG. 5, lane 2;versus 8) avoiding the co-purification of inactive immature fX molecules. After addition of 10 mM EDTA, 0,1% of Tween 80, 0,1 mM Pefabloc and adjustment of the pH to 7,4, the supenatant was loaded onto a Fractogel EMD TMAE 650 (M) column equilibrated with Buffer A (20 mM Tris, 120 mM NaCl, 10 mM EDTA, 0,1% Tween 80, pH7,4). The column was washed with 20 mM Tris, 180 mM NaCl, 0,1% Tween 80, pH 7,4. rfX Molecules were eluted with Buffer C (20 mM Tris, 150 mM NaCl, 10 mM CaCl2, 0,1% Tween, pH 7,4). The Western Blot analysis of the different purification fractions (FIG. 5) shows that almost all rfX/fXI(Q-R/I) molecules of the elution fraction are present in form of the mature double chain (HC, LC; lane 6), similarly to purified plasma fX (lane7). In order to inhibit residual amounts of rfXa potentially present, which could have been formed during cell culture or the purification procedure, the elution fraction was subsequently treated with 10 μM ERGck (Hematological Technologic Inc.), a specific fXa inhibitor. Excess of this inhibitor was removed by the subsequent diafiltration step with 10 mM Tris, 8 g/L NaCl, 4 g/L NaCitrate, 0,01% Tween 80, pH7. The preparation was stored at −80° C. until use. The same purification procedure was used for the preparation of rfX wild-type employed as a control in the following experiments.

a. Determination of the Functional activity of purified rfX/fXIa(Q-R/I) in human and murine fVIII- and fIX-deficient plasma In order to confirm the functional activity of the purified rfX/fXIa(Q-R/I) molecules, the aPTT (Activated Partial Thromboplastin Time) in FVIII- and fIX-deficient plasma from human and murine origin was measured in the presence of the rfX molecules. 100 μl of deficient plasma (immunodepleted human plasma, Baxter AG; plasma from fVIII or fIX knock-out mice) was mixed with 50 μl of a 10 μg/ml purified fX molecule preparation (see above), 150 μl DAPPTIN (Baxter AG) and incubated for 3 min at 37° C. The coagulation reaction was initiated by 150 μl 25 mM CaCl$_2$. The clotting time was estimated as described in example 3. The percentage of activity was determined by using a standard curve Log (% activity) versus Log (clotting time). For the standard curve, 100 μl of 100%, 80% 50%, 25% or 12,5% human or murine reference plasma was mixed to 50 μl of the fX buffer and 150 μl DAPPTIN and incubated for 3 min at 37° C. The initiation of coagulation and estimation of clotting time was performed as described above. The reference plasmas consist of normal human plasma (Baxter AG) or plasma pool from normal mice mixed at different ratios with the corresponding fVIII or fIX deficient plasmas. The clotting time as well as the percentage of activity compared to normal plasma are given in table 4. The results show that a significant reduction of the clotting time is mediated by purified rfX/fXIa(Q-R/I) in all deficient plasma tested either from human or murine origin. A normalization of the aPTT is even observed in human and murine fIX-deficient plasma and in murine fVIII-deficient plasma. In contrast to the rfX-analogue, rfX wt molecules at the corresponding concentrations do not mediate a significant reduction of the clotting time in these plasmas. Furthermore, the normalization of the aPTT in deficient mice plasma indicates that the rfX/fXIa(Q-R/I) molecules are able to interact with the corresponding murine coagulation proteins mediating the fVIII and fIX bypass activity observed in vitro in human plasma, a prerequisite for testing these molecules in vivo in a mouse animal model.

b. Functional Activity of the rfX/fXIa(Q-R/I) Variant in Vivo

The functionality of rfX/fXIa(Q-R/I), as a molecule exhibiting a fVIII bypass activity, was tested in vivo by using fVIII knock-out mice (Table 5). The validity of the fVIII knock out mice as an animal model system for testing fVIII bypass

TABLE 4

Functional Activity of purified rfX/fXIa(Q-R/I) in human fVIII and fIX-deficient plasma and in plasma from fVIII and fIX Knock-Out mice

|  | Normal Plasma | FVIII-def. Plasma | FVIII-def. Plasma + rfX wt | FVIII-def. Plasma + rfX/fXIa(Q-R/I) | FIX-def. Plasma | RfIX-def. Plasma + rfX wt | FIX-def. Plasma + rfX/fXIa(Q-R/I) |
|---|---|---|---|---|---|---|---|
| Coagulation Time in sec. | 52.3 | 138.5 | 112.7 | 52.5 | 153.7 | 117.5 | 48.6 |
| % Activity in mouse plasma | 100 | — | 3.7 | 97 | — | 0.1 | 166 |
| Coagulation Time in sec. | 47.5 | 143.9 | 118.3 | 56.3 | 161.6 | 117.9 | 48 |
| % Activity in human plasma | 100 | — | 2.4 | 77 | — | 0.5 | 99 | activity was controlled by using the commercially available plasma derived FEIBA preparation (Baxter AG). As a negative control, a preparation of purified rfX wt was used. In order to compare the effect of rfX/fXIa (Q-R/I) and rfXwt the unit definition for the dose to be administered was based on the fX activity determined in PT (prothrombin time) assay. For the PT assay, 100 µl of fX molecule preparation and 100 µl fx-deficient plasma (Baxter AG) was incubated for 2 min at 37° C. The coagulation was initiated by 100 µl of Calcium/Thromboplastin mixture (Baxter AG). The clotting time was estimated as described in example 3. The fX activity in units was determined by using a standard curve established with a fX reference standard (Baxter AG). The preparations were administered intravenously under anesthesia at the indicated dose in U/kg (table 5). 30 min after injection the bleeding was induced by cutting the tail at a distance of 1 cm from its end. The survival rate of the animals after 48 hours serves as a parameter for functionality. The significant reduction of mortality observed for the animals treated with FEIBA, demonstrates that fVIII knock-out mice represent a suitable model system. None of the animals treated with 300 U rfXwt/kg survived, a result to be expected from the in vitro findings. However, the application of rfX/fXIa(Q-R/I) at 300 U/kg resulted in a significant improvement of the survival rate (60%). This result demonstrated that the rfx-analogue molecules exhibit a significant fVIII bypass activity in vivo, at the dosage used.

TABLE 5

Determination of the survival rate of fVIII knock-out mice treated with rfX/fXIa(Q-R/I) variant and rfX wt

|  | FEIBA 300 U/kg | FEIBA 150 U/kg | rfX/fXI(Q-R/I) 300 U/kg | RfX wt 300 U/kg |
|---|---|---|---|---|
| Survival | 3/3 | 1/2 | 6/10 | 0/3 |
| % Survival | 100 | 50 | 60 | 0 |

In conclusion, the functional properties of the rfX/fXIa (Q-R/I) molecule described in these experiments, demonstrate that it represents a prime candidate for the development of a alternate therapeutic agent for the treatment of hemophiliacs having developed inhibitory antibodies.

What is claimed is:

1. A Factor X analog which contains one or more modifications in SEQ ID NO:2 selected from the group consisting of:
   a) Ile235 is Val or Ala;
   b) Thr233 is Ser or Asn;
   c) Leu232 is Phe, Arg or Ile;
   d) Asn231 is Asp, Lys, Thr, or Glu;
   e) Asn230 is Ser, Lys, Met, Thr, or Asp;
   f) Asp229 is Phe, Thr, Ser, Pro, Leu, or Ile;
   g) Gly228 is Ser, Gln, Ile, Thr, Asn, or Pro; and
   h) Arg227 is Gln, Ser, His, Tyr, or Glu.

2. The Factor X analog of claim 1, wherein the amino acid sequence of residues 227–233 is Gln227-Ser228-Phe229-Asn230-Asp231-Phe232-Thr233 (SEQ ID NO:17).

3. The Factor X analog of claim 1, wherein the amino acid sequence of residues 227–233 is Ser227-Gln228-Thr229-Ser230-Lys231-Leu232-Thr233 (SEQ ID NO:18).

4. The Factor X analog of claim 1, wherein the modification forms a processing site for Factor XIa or a derivative thereof.

5. A Factor X analog which
   (i) contains one or more modifications in SEQ ID NO:2 selected from the group consisting of:
      a) Ile235 is Val or Ala;
      b) Thr233 is Ser or Asn;
      c) Leu232 is Phe, Arg or Ile;
      d) Asn231 is Asp, Lys, Thr, or Glu;
      e) Asn230 is Ser, Lys, Met, Thr, or Asp;
      f) Asp229 is Phe, Thr, Ser, Pro, Leu, or Ile;
      g) Gly228 is Ser, Gln, Ile, Thr, Asn, or Pro; and
      h) Arg227 is Gln, Ser, His, Tyr, or Glu; and
   (ii) has a further modification occurring at Lys370 and/or within a segment extending from Arg 469 to Ser476 of SEQ ID NO:2.

6. The Factor X analog of claim 1, wherein said modification permits an in vivo activation of the Factor X analog into native Factor Xa or a Factor Xa analog.

7. The Factor X analog of claim 1, wherein said modification permits an in vitro activation of the Factor X analog into native Factor Xa or a Factor Xa analog.

8. The Factor X analog of claim 1 that contains an intact β-peptide.

9. The Factor X analog of claim 1 which is in the form of a double-chain molecule.

10. The Factor X analog of claim 1 having a shortened C-terminal region, wherein the C-terminal region corresponds to amino acid residues 476–487.

11. A preparation comprising the Factor X analog of claim 1 or a precursor protein thereof.

12. The preparation of claim 11, wherein the modification forms a cleavage site for Factor XIa or a derivative thereof.

13. The preparation of claim 11, wherein the Factor X analog is a Factor Xα analog.

14. The preparation of claim 11, wherein the Factor X analog has a shortened C-terminal amino acid sequence, wherein the C-terminal region corresponds to amino acid residues 476–487.

15. The preparation of claim 11, wherein the Factor X analog is a double-chain molecule.

16. The preparation of claim 11, wherein the Factor X analog is a single-chain Factor X analog in enzymatically inactive form that is at least 80% pure; and the preparation does not contain inactive proteolytic intermediates of Factor X/Xa analog.

17. The preparation of claim 11, wherein the Factor X analog is a single-chain molecule.

18. The preparation of claim 11, wherein the modification permits an in vivo activation of the Factor X analog into native Factor Xa or a Factor Xa analog.

19. The preparation of claim 11, wherein the modification permits an in vitro activation of the Factor X analog into native Factor Xa or into a Factor Xa analog.

20. The preparation of claim 11 that is formulated as a pharmaceutical preparation.

21. A method for obtaining a preparation comprising an activated Factor X analog, the method comprising:

(a) providing the Factor X analog of claim 1; and (b) activating the Factor X analog to obtain the activated Factor X analog.

22. The method of claim 21, further comprising formulating the preparation with a physiologically acceptable matrix.

23. The method of claim 21, further comprising combining the preparation with a blood factor or an activated form of a blood factor as an additional component.

24. The method of claim 23, wherein the additional component comprises at least one component with Factor VIII inhibitory bypass activity.

25. The preparation of claim 11 that is formulated as a pharmaceutical compound and present as a multi-component preparation.

26. A method for preparing a pharmaceutical composition, comprising formulating the preparation of claim 11 as pharmaceutical composition.

27. The Factor X analog as set forth in claim 5, wherein the further modification is a substitution located at the β-peptide cleavage site located between Arg469 and Gly470 of SEQ ID NO:2.

28. The Factor X analog as set forth in claim 5, wherein the further modification is selected from a mutation, a deletion and an insertion between amino acid positions Arg469 and Ser476 of SEQ ID NO:2.

29. A Factor X analog which (i) contains one or more modifications in SEQ ID NO:2 selected from the group consisting of:
 a) Ile235 is Val or Ala;
 b) Thr233 is Ser or Asn;
 c) Leu232 is Phe, Arg or Ile;
 d) Asn231 is Asp, Lys, Thr, or Glu;
 e) Asn230 is Ser, Lys, Met, Thr, or Asp;
 f) Asp229 is Phe, Thr, Ser, Pro, Leu, or Ile;
 g) Gly228 is Ser, Gln, Ile, Thr, Asn, or Pro; and
 h) Arg227 is Gln, Ser, His, Tyr, Glu; and (ii) has a further modification which is a deletion of Factor X β-peptide (Gly470 to Lys488 of SEQ ID NO:2).

* * * * *